(12) United States Patent
Barve et al.

(10) Patent No.: US 12,658,289 B2
(45) Date of Patent: Jun. 16, 2026

(54) SYSTEMS AND METHODS FOR RETRIEVING CLINICAL INFORMATION BASED ON CLINICAL PATIENT DATA

(71) Applicant: nference, inc., Cambridge, MA (US)

(72) Inventors: Rakesh Barve, Bangalore (IN); Akash Anand, Bhagalpur (IN); Shishir Gowda, Toronto (CA); Sairam Bade, Ameenabad Anathagiri Suryapet (IN); Purushottam Sinha, Gaya (IN)

(73) Assignee: nference, Inc., Cambridge, MA (US)

( * ) Notice: Subject to any disclaimer, the term of this patent is extended or adjusted under 35 U.S.C. 154(b) by 469 days.

(21) Appl. No.: 17/500,621

(22) Filed: Oct. 13, 2021

(65) Prior Publication Data

US 2022/0115100 A1 Apr. 14, 2022

Related U.S. Application Data

(60) Provisional application No. 63/126,974, filed on Dec. 17, 2020.

(30) Foreign Application Priority Data

Oct. 14, 2020 (IN) .............................. 202041044674

(51) Int. Cl.
*G16H 10/60* (2018.01)
*G06F 16/903* (2019.01)

(52) U.S. Cl.
CPC ....... *G16H 10/60* (2018.01); *G06F 16/90335* (2019.01)

(58) Field of Classification Search
CPC .......................... G16H 10/60; G06F 16/90335
See application file for complete search history.

(56) References Cited

U.S. PATENT DOCUMENTS 6,601,026 B2 * 7/2003 Appelt .................. G06F 16/313
707/E17.084
10,224,119 B1 * 3/2019 Heinrich ................ G16H 50/70
(Continued)

FOREIGN PATENT DOCUMENTS

CN 110998740 A * 4/2020 ........... G06F 16/243
WO WO-2019071098 A2 * 4/2019 ........... A61K 31/137

OTHER PUBLICATIONS

M. J. Islam, J. Rahman and M. K. Ben Islam, "Improving Patient Cohort Identification using Neural Word Embedding with Structured Analysis," ICECTE, Rajshahi, Bangladesh, 2019, pp. 5-8, doi: 10.1109/ICECTE48615.2019.9303568. (Year: 2019).*

(Continued)

*Primary Examiner* — Jason S Tiedeman
*Assistant Examiner* — Jonathan C Edouard
(74) *Attorney, Agent, or Firm* — CALDWELL LLC

(57) ABSTRACT

Disclosed systems, methods, and computer readable media can retrieve clinical information based on clinical patient data. For example, a method for retrieving clinical information based on clinical patient data includes receiving a specification of a patient cohort, receiving a query, retrieving a list of search results based on the query and the specification of the patient cohort, computing one or more inferences for each item in the list of search results, providing an aggregate statistical analysis associated with the one or more inferences, and providing, by the one or more hardware processors, a response to the query that includes the aggregate statistical analysis. Each element in the list of search results comprises at least a portion of a clinical data record associated with a patient in the patient cohort.

20 Claims, 14 Drawing Sheets

(56) References Cited

U.S. PATENT DOCUMENTS

| | | | | |
|---|---|---|---|---|
| 10,643,751 | B1 * | 5/2020 | Drouin | G16H 50/70 |
| 2008/0120296 | A1 * | 5/2008 | Kariathungal | G16H 10/60 |
| 2008/0243825 | A1 | 10/2008 | Staddon et al. | |
| 2011/0225155 | A1 | 9/2011 | Roulland et al. | |
| 2015/0006456 | A1 * | 1/2015 | Sudharsan | G16H 40/63 |
| | | | | 706/46 |
| 2015/0248494 | A1 | 9/2015 | Mital et al. | |
| 2016/0019666 | A1 | 1/2016 | Amarasingham et al. | |
| 2018/0039904 | A1 * | 2/2018 | Stevens | G06N 20/00 |
| 2018/0046764 | A1 * | 2/2018 | Katwala | G16H 15/00 |
| 2019/0163679 | A1 * | 5/2019 | Srinivasa | G16H 50/70 |
| 2019/0206522 | A1 * | 7/2019 | Baldwin | G06F 16/382 |
| 2019/0258950 | A1 * | 8/2019 | Birnbaum | G16H 10/20 |
| 2019/0354883 | A1 | 11/2019 | Aravamudan et al. | |
| 2020/0057767 | A1 * | 2/2020 | Shah | G06F 16/2255 |
| 2020/0211716 | A1 * | 7/2020 | Lefkofsky | G06F 18/214 |

OTHER PUBLICATIONS

CN-110998740-A—translated (Year: 2020).*
Liu, Sijia, et al. "Implementation of a Cohort Retrieval System for Clinical Data Repositories Using the Observational Medical Outcomes Partnership Common Data Model: Proof-of-Concept System Validation." Oct. 2020, p. e17376. DOI.org (Crossref), https://doi.org/10.2196/17376. (Year: 2020).*
International Search Report and Written Opinion issued by U.S. Patent and Trademark Office as International Searching Authority in International Application PCT/US21/54790 dated Jan. 24, 2022 (8 pages).

* cited by examiner

100

200

Information retrieval 204

| Search 230 | Statistical analysis 240 | Machine learning 250 |

| Knowledge base 220 | Controller 210 | Inference database 260 |

Application 202

400

| 410 | Receive a specification of a patient cohort |
|---|---|

| 420 | Receive a query |
|---|---|

| 430 | Expand the query to include one or more related terms |
|---|---|

| 440 | Retrieve a list of search results based on the expanded query |
|---|---|

| 450 | Identify one or more entities within the list of search results |
|---|---|

| 460 | Compute one or more inferences for each item in the list of search results |
|---|---|

| 460 | Provide an aggregate statistical analysis associated with the one or more inferences |
|---|---|

| 470 | Provide a response to the query that includes the aggregate statistical analysis |
|---|---|

FIG. 4

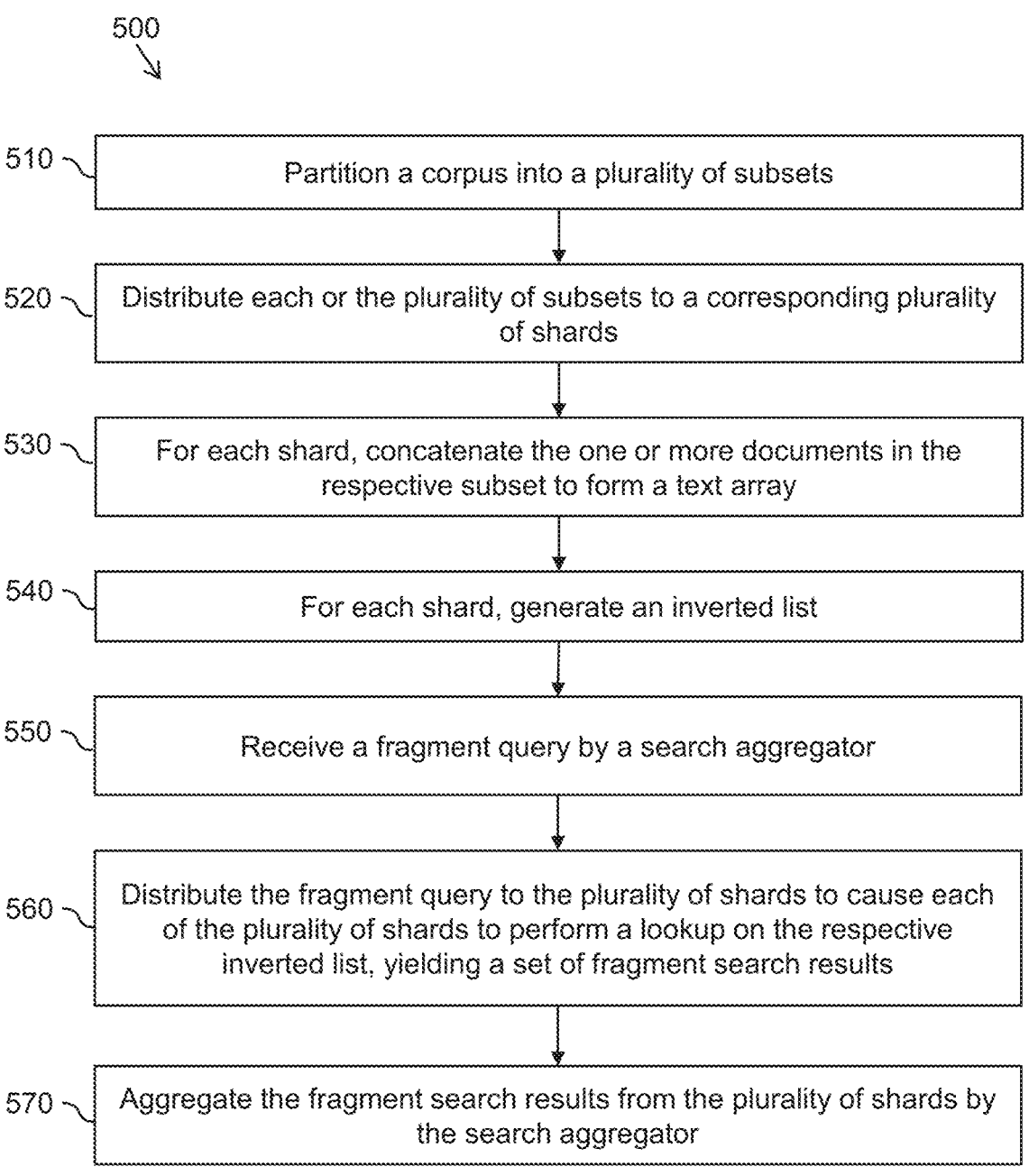

500

510 — Partition a corpus into a plurality of subsets

520 — Distribute each or the plurality of subsets to a corresponding plurality of shards 530 — For each shard, concatenate the one or more documents in the respective subset to form a text array 540 — For each shard, generate an inverted list 550 — Receive a fragment query by a search aggregator 560 — Distribute the fragment query to the plurality of shards to cause each of the plurality of shards to perform a lookup on the respective inverted list, yielding a set of fragment search results 570 — Aggregate the fragment search results from the plurality of shards by the search aggregator

FIG. 5

Timestamped Rows R0, R1 if temporally co-occurring data...

| | Physician Notes | Other Notes and Reports | L1 | Lt2 | ... | DIAG Desc | Diag Code | Chord ICD | Mapped Dis. | : | Meds Adm. | Fact Orders | EES Drug | Drug Class | ... | ECG | ECHO.. | DEM |
|---|---|---|---|---|---|---|---|---|---|---|---|---|---|---|---|---|---|---|
| | | | Lab tests | | | Diagnosis, Diseases | | | | | Drugs | | | | | Other Data... | | |
| $R_0$ | | 622 | 631 | 632 | 639 | 641 | 642 | 643 | 644 | 649 | 651 | 652 | 653 | 654 | 659 | 661 | 662 | 663 |
| $R_1$ | | | | | | | | | | | | | | | | | | 669 |
| $R_2$ | | | | | | | | | | | | | | | | | | |
| ... | | | | | | | | | | | | | | | | | | |

611  
612  
619

Text and Associated Data — Unstructured Notes, Reports

Numeric

Categorical, Short Text — Augmented Data (heuristics)

FIG. 6

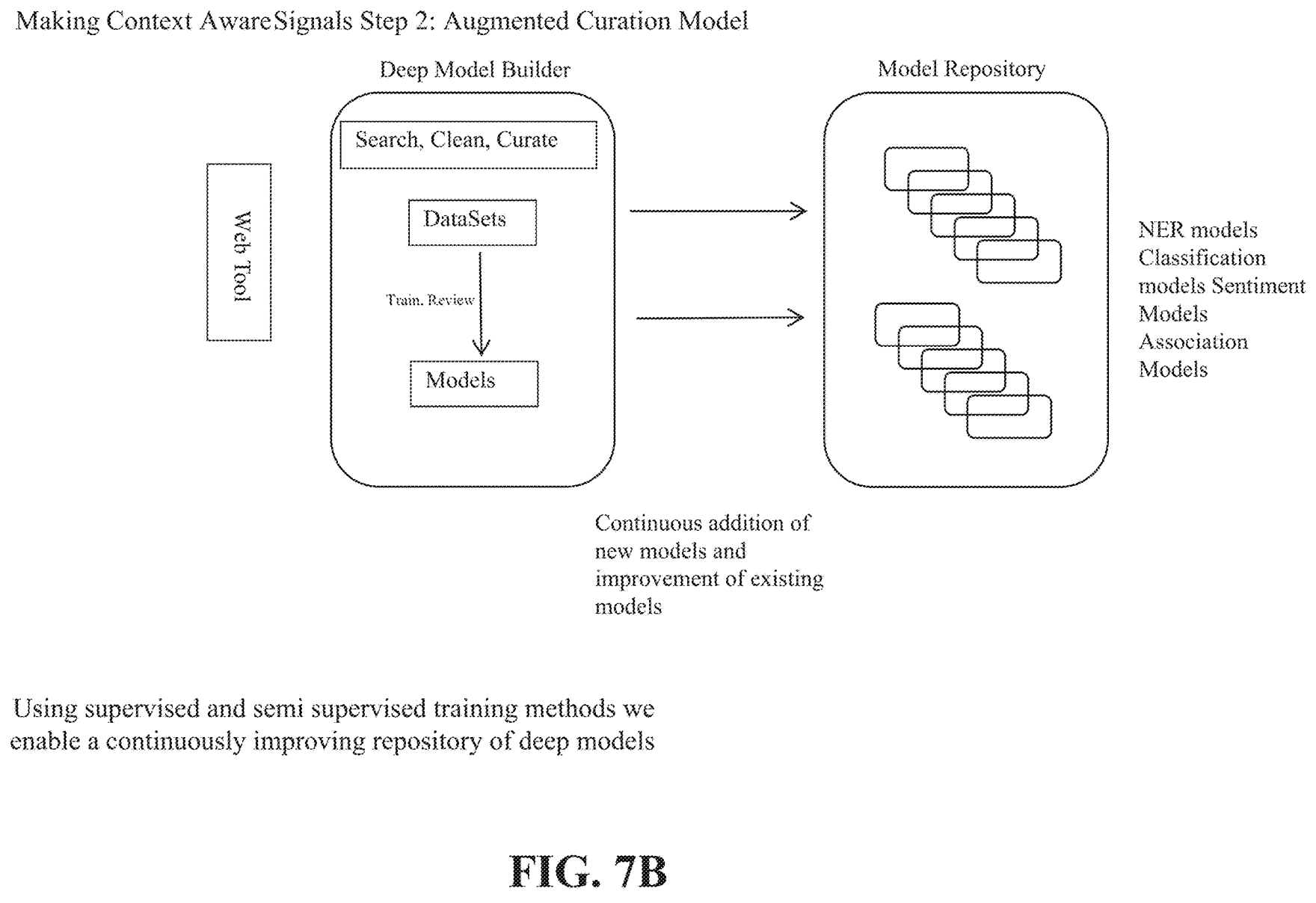

Making Context AwareSignals Step 2: Augmented Curation Model

Model Repository

NER models
Classification
models Sentiment
Models
Association
Models

Deep Model Builder

Search, Clean, Curate

DataSets

Tran. Review

Models

Web Tool

Continuous addition of
new models and
improvement of existing
models

Using supervised and semi supervised training methods we
enable a continuously improving repository of deep models

FIG. 7B

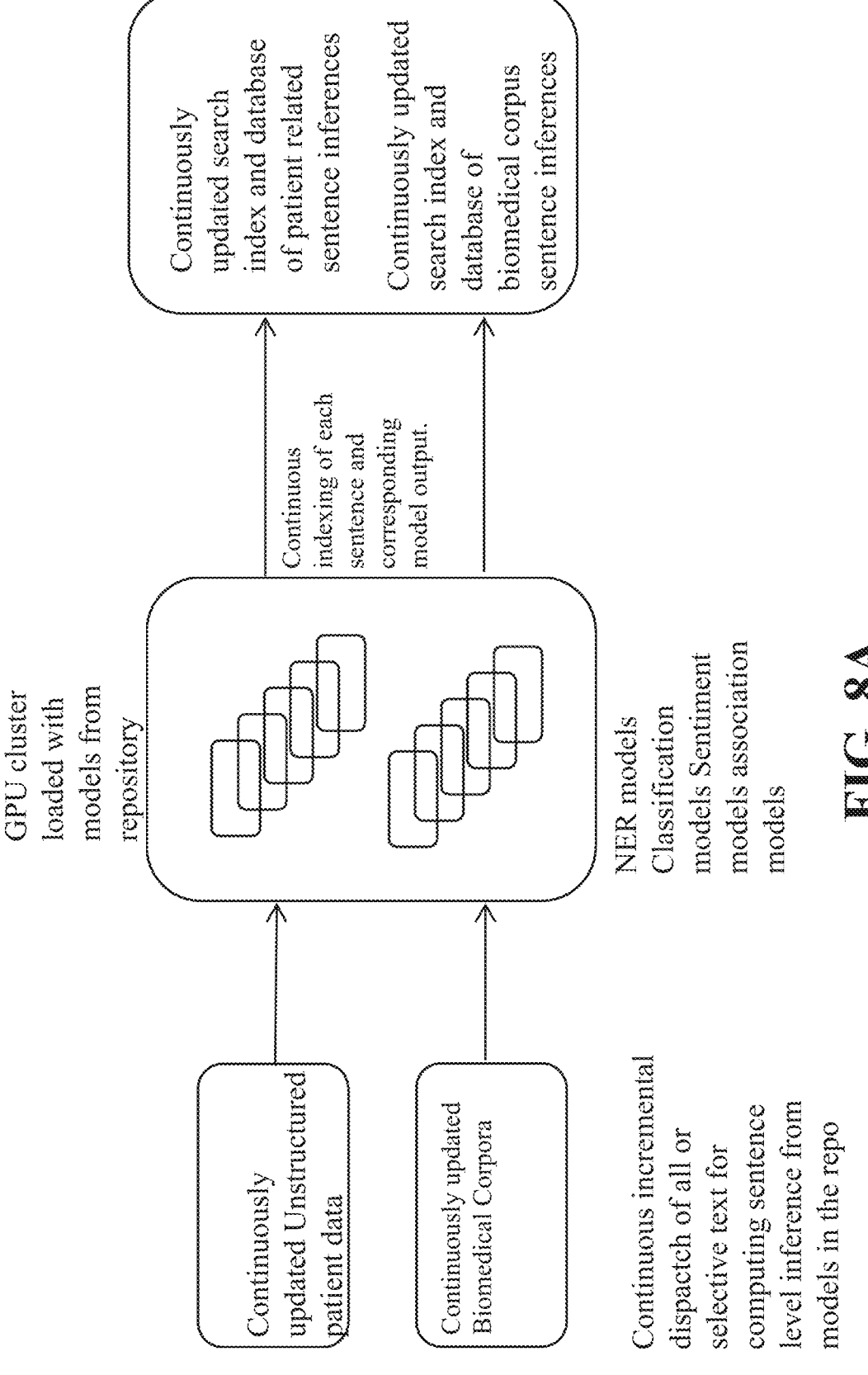

Step 2: Continuous computing for making sentence level inference database

GPU cluster loaded with models from repository

Continuously updated Unstructured patient data

Continuously updated Biomedical Corpora

Continuous incremental dispatch of all or selective text for computing sentence level inference from models in the repo NER models Classification models Sentiment models association models Continuous indexing of each sentence and corresponding model output.

Continuously updated search index and database of patient related sentence inferences Continuously updated search index and database of biomedical corpus sentence inferences

Interactive Clinical Cohort Query Analysis and Data Flow Execution Engine

1030

High performance information retrieval engine

| Indexing search of text fragments and localized records | Biomedical Knowledge Graph & Semantics Engine | Indexing and Search of other raw data | Indexing and Search of pre-computed inference | Temporal indexing and organization of patient data | Cohort level aggregation comparison & statistics engine |

1020

AI & Statistical Inference Continuous Computing

| Continuously evolving set of Deep Neural Network and other statistical models | Continuous Computing of model inference on localized text fragments from notes, individual images, localized patient info etc. | Continuous computing of whole patient level/higher level inference models built on top of lower level inference models |

1010

Continuously crawled holistic longitudinal clinical patient data

| Patient notes, Physician narratives, hospital notes | ECG reports, Pathology reports, Radiology reports | ECGs, Pathology, Radiology images | Diagnosis medication records, lab tests, procedure records | Hospitalization data, ICU and inpatient stay records | Genome sequencing and molecular data |

FIG. 10

1000
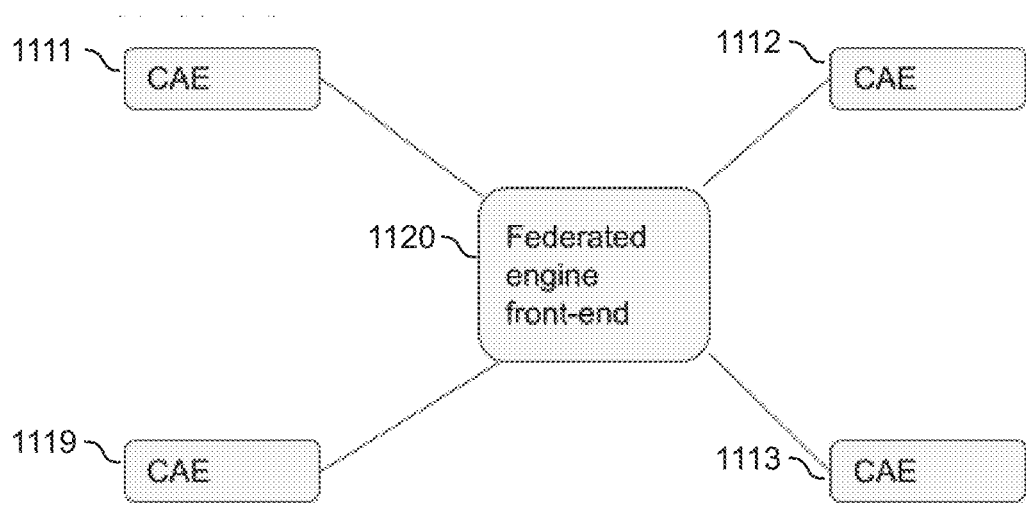
1111 — CAE
1112 — CAE
1120 — Federated engine front-end
1119 — CAE
1113 — CAE
FIG. 11

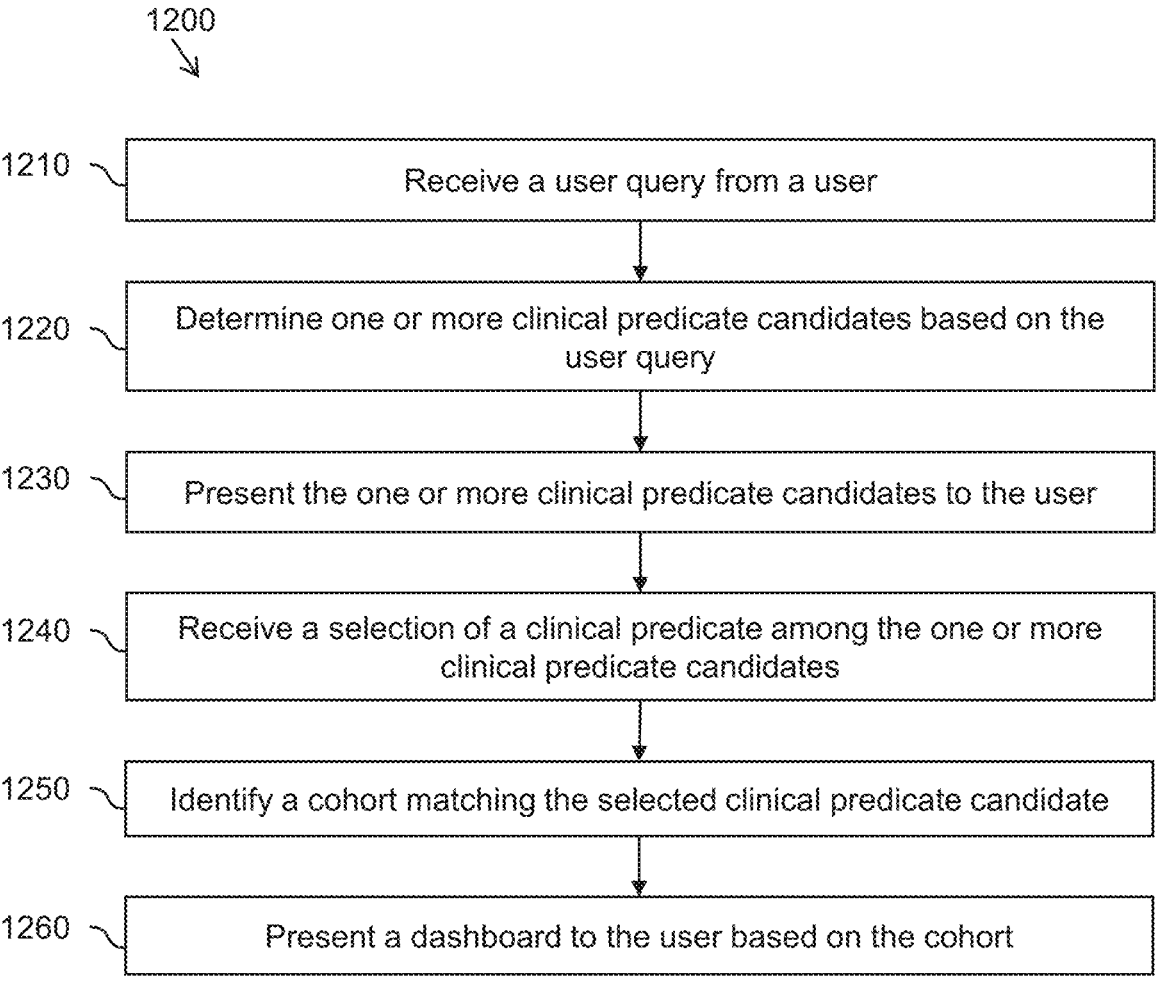

1200

1210 — Receive a user query from a user

1220 — Determine one or more clinical predicate candidates based on the user query 1230 — Present the one or more clinical predicate candidates to the user 1240 — Receive a selection of a clinical predicate among the one or more clinical predicate candidates 1250 — Identify a cohort matching the selected clinical predicate candidate 1260 — Present a dashboard to the user based on the cohort

FIG. 12

SYSTEMS AND METHODS FOR RETRIEVING CLINICAL INFORMATION BASED ON CLINICAL PATIENT DATA

RELATED APPLICATIONS

This application claims priority under 35 U.S.C. § 119(e) to U.S. Provisional Application No. 63/126,974, entitled "Systems and Methods for Retrieving Clinical Information Based on Clinical Patient Data," filed Dec. 17, 2020, and under 35 U.S.C. § 119(a) to Indian Provisional Patent Application No. 202041044674, entitled "Systems and Methods for Retrieving Clinical Information Based on Clinical Patient Data," filed Oct. 14, 2020, each of which is incorporated by reference herein in its entirety.

TECHNICAL FIELD

This application relates generally to digital analysis of clinical data and specifically to techniques for retrieving clinical information based on clinical patient data.

BACKGROUND

Search engines, and other types of information retrieval systems, have emerged as powerful tools for accessing documents and records in a corpus. Search engines can operate on local repositories or over distributed networks, and can evaluate and rank results based on the contents of documents, network graphs, and the like.

In general, search engines retrieve documents and records from a corpus in response to a query. The query can include one or multiple text phrases and can include various other criteria that set the parameters for the search that the user desires to perform. Where the query includes multiple phrases, the phrases can be logically combined using, e.g., Boolean operators (AND, OR, NOT).

Moreover, in recent years more and more clinical patient data has become digitized and available for information retrieval tasks. Accordingly, it is desirable to develop improved techniques for retrieving clinical information based on clinical patient data.

BRIEF DESCRIPTION OF THE DRAWINGS

FIG. 4 is a simplified diagram of a method for retrieving clinical information based on clinical patient data according to some embodiments.

FIG. 5 is a simplified diagram of a method for performing a fragment search according to some embodiments.

FIG. 6 is a simplified diagram of a data table storing patient clinical data according to some embodiments.

FIGS. 7A and 7B are simplified diagrams of a machine learning model builder application according to some embodiments FIGS. 8A and 8B are simplified diagrams of a data flow for populating an inference database according to some embodiments.

FIG. 10 is a simplified diagram of a system for cohort analysis according to some embodiments.

FIG. 11 is a simplified diagram of an information retrieval system implementing a federated protocol according to some embodiments.

FIG. 12 is a simplified diagram of a method for information retrieval using a cohort analysis system according to some embodiments.

Figure 1:
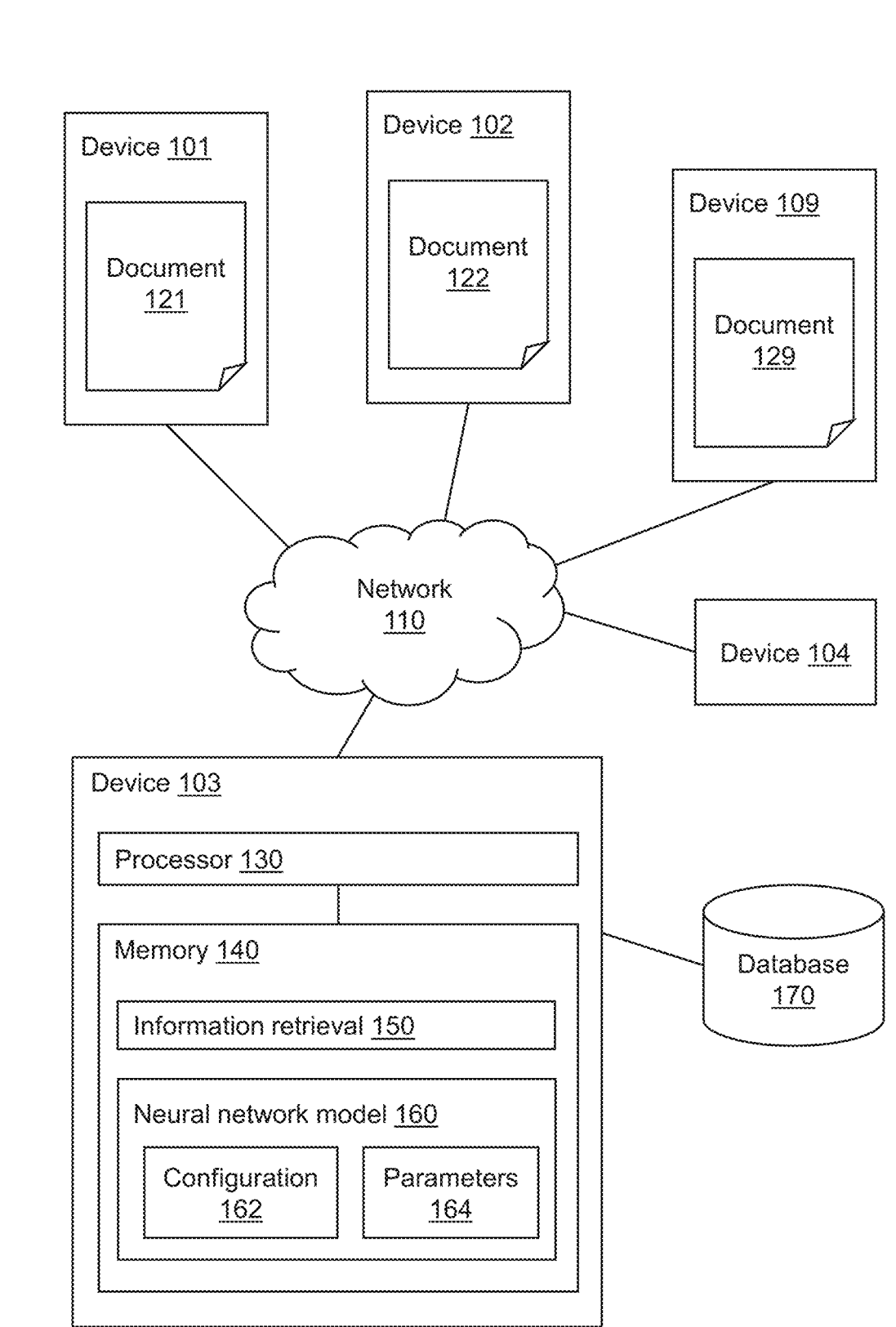
FIG. 1 is a simplified diagram of a system for information retrieval according to some embodiments.

Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

Over the past several years more and more clinical patient data (especially in the U.S.) has become digitized, and significant progress has been made in building systems that preserve patient privacy via AI based de-identification and cloud based data science "sandbox" systems for furthering biomedical and pharmacological research. Accordingly, biomedical and pharmacological researchers as well as clinical practitioners can benefit from "internet-style" information retrieval tools germane to biomedical, pharmacological and clinical work.

Retrieving information that is responsive to a search query from a repository of information, such as a repository of clinical patient data, can be challenging. Information can be stored in a variety of ways, such as in a collection of documents, a database (e.g., a structured, semi-structured, or unstructured database), a knowledge graph, or the like. Some information retrieval tools are designed to retrieve documents or other records from a repository based on a query term. For example, various publicly available search engines (e.g., Google or PubMed) are configured to identify web pages, journal articles, books, etc. that are relevant to a user-provided query term.

However, in some scenarios, identifying relevant records in a repository may not yield an adequate response to a user's query. For example, when the user is seeking to make a determination or inference based on aggregated information (e.g., to determine whether a particular drug has been shown to be effective against a particular disease based on an aggregate of clinical records that reference the drug), search results that include a list of relevant documents may not clearly and directly respond to the user's query. To illustrate, in the above example of a user seeking an answer to whether a particular drug has been shown to be effective against a particular disease, the user may be left with the onerous task of browsing each relevant document (e.g., each clinical data record that mentions the drug and the disease) to determine which documents are in fact responsive to the query. Subsequent manual analysis of the responsive documents may then be performed to yield the answer to the initial question posed by the user. This process of manually examining search results to piece together the desired information and make a suitable determination or inference tedious and time-consuming.

Accordingly, it is desirable to develop improved techniques for retrieving information that is responsive to a query, particularly techniques that can be applied to information stored in clinical data records.

To address these challenges, the present disclosure describes systems and methods to effectively search, mine and retrieve sound information from vast troves of patient data with ease of use and responsiveness comparable to internet-style information retrieval tools such as web search engines. In some embodiments, the systems and methods may be implemented as a web scale federated 'clinical sentiment' search engine using clinical patient data that provides information retrieval services with the ease of use associated with internet tools but with responses specialized to clinical, biomedical and pharmacological applications. Illustrative questions that may be addressed include questions such as the following:

a) How many patients have neuromyelitis optica?
 b) What is the typical standard of care for people afflicted by a particular kind of breast cancer?
 c) How effective is drug X compared to drug Y for treatment of a disease which is an indication to both?
 d) How many patients afflicted with a disease D and who have been subject to a certain drug or intervention have positive outcomes?
 e) To what extent is it true that patients treated with drug X develop disease D an adverse side effect?
 f) What is the fraction of patients afflicted with disease D end up after treatment having re-admission versus a genuine improved standard of life?
 g) What is the quality of life during treatment for medication X versus medication Y?
 h) Which drug is more effective, which drug has lesser side effects, as seen in actual patient data?

It is further desirable to enable clinical and pharmacological practitioners to obtain answers to such questions in a quantitative and statistically sound manner, with the ease of use of internet tools. The present disclosure describes a system that may be configured to answer such questions and, additionally or alternatively, may enable projecting the real-world prevalence of disease conditions, effectiveness of interventions in terms of outcomes as well as performance of institutions.

Additionally, biological systems such as the human body generally do not behave according to physical theories that from first principles explain biological observations and measurements, unlike the physics of inanimate systems. In order to make progress in this science of biological systems, clinicians and pharmacologists can benefit from looking upon retrospective clinical patient records as observations in physician-directed experiments involving interventions, diseases, diagnoses and explicit laboratory measurements reflecting and evaluating the knowledge and understanding of physicians. This experimental science view influences the types of data and techniques for data processing that may be used for information retrieval. In clinical and pharmacological applications, for example, relevant information may include but aren't limited to (a) the genuine prevalence of a specific disease in a given set of patients, (b) the typical conditions in which physicians administer a specific medication or in which an administered medication is quantifiably less effective, (c) confounders that may lead to a specific adverse event caused by a drug being administered for a specific disease, and (d) the typical disease or phenotypic progression over time. In each situation, the researcher may typically seek a list of deidentified patient identifiers from the data to serve as the 'evidence' backing the returned information, and the hypothesis-free enrichment of any medicine related attribute of that set of patients. Owing to the nature of the data, such information and evidence is not available on the internet.

Temporal trends within a patient, or shared temporal trends in a set of similar patients may have a significant impact in clinical and pharmacological applications relative to other application domains. For example, each patient's data consists of a time series of unstructured data (narrative physician notes, reports of various kinds) interspersed with other clinically relevant structured and semi-structured data such as laboratory tests, diagnosis codes, recorded medications and procedures, and so on.

In view of these characteristics of clinical and pharmacological applications, in some embodiments, clinical data may be analyzed using domain specific AI based analysis of patient data. These domain specific AI models may be applied to a combination of unstructured as well as structured data within the clinical patient data systems, and may also incorporate other biomedical knowledge. In some embodiments, the AI models may be tailored to disease areas, therapeutic modalities and combinations of these FIG. 1 is a simplified diagram of a system 100 for information retrieval according to some embodiments. System 100 includes a plurality of devices 101-109 that are communicatively coupled via a network 110. Devices 101-109 generally include computer devices or systems, such as personal computers, mobile devices, servers, or the like. Network 110 can include one or more local area networks (LANs), wide area networks (WANs), wired networks, wireless networks, the Internet, or the like. Illustratively, devices 101-109 may communicate over network 110 using the TCP/IP protocol or other suitable networking protocols.

One or more of devices 101-109 can store digital documents 121-129 and/or access digital documents 121-129 via network 110. For example, as depicted in FIG. 1, devices 101, 102, and 109 store digital documents 121, 122, and 129, respectively, and device 103 accesses digital documents 121-129 via network 110. Digital documents 121-129 can include webpages, digital files, digital images (including one or more frames of a video or an animation), or the like. Illustratively, digital documents 121-129 can be formatted as HTML/CSS documents, PDF documents, word processing documents (e.g., Word documents), text documents, slideshow presentations (e.g., PowerPoint presentations), image files (e.g., JPEG, PNG, or TIFF images), or the like. Digital documents 121-129 can be heterogeneous (e.g., of different formats or file types) or homogenous (e.g., of the same format or file type), and can include structured or unstructured data. In general, digital documents 121-129 include text data, which can include alphanumeric characters, symbols, emojis, image representations of text, or the like. For efficient storage and/or transmission via network 110, documents 121-129 may be compressed prior to or during transmission via network 110. Security measures such as encryption, authentication (including multi-factor authentication), SSL, HTTPS, and other security techniques may also be applied.

According to some embodiments, device 103 may access one or more of digital documents 121-129 by downloading digital documents 121-129 from devices 101, 102, and 109. Moreover, one or more of devices 101, 102, or 109 can upload digital documents 121-129 to device 103. Digital documents 121-129 may be updated at various times. Accordingly, device 103 may access digital documents 121-129 multiple times at various intervals (e.g., periodically) to obtain up-to-date copies.

As depicted in FIG. 1, device 103 includes a processor 130 (e.g., one or more hardware processors) coupled to a memory 140 (e.g., one or more non-transitory memories). Memory 140 stores instructions and/or data corresponding to an information retrieval program 150. When executed by processor 130, information retrieval program 150 causes processor 130 to perform operations associated with retrieving information responsive to a query. In some embodiments, the query may be provided as an input (e.g., a query string) by a user of device 104 and transmitted to device 103 via network 110. Subsequently, a response to the query determined using information retrieval program 150 may be delivered via network 110 to device 104 and rendered to the user via a user interface. Illustrative embodiments of data flows implemented by information retrieval program 150 are described in further detail below with reference to FIGS. 2-3.

During execution of information retrieval program 150, processor 130 may execute one or more neural network models, such as neural network model 160. Neural network model 160 is trained to make predictions (e.g., inferences) based on input data. Neural network model 160 includes a configuration 162, which defines a plurality of layers of neural network model 160 and the relationships among the layers. Illustrative examples of layers include input layers, output layers, convolutional layers, densely connected layers, merge layers, and the like. In some embodiments, neural network model 160 may be configured as a deep neural network with at least one hidden layer between the input and output layers. Connections between layers can include feed-forward connections or recurrent connections.

One or more layers of neural network model 160 is associated with trained model parameters 164. The trained model parameters 164 include a set of parameters (e.g., weight and bias parameters of artificial neurons) that are learned according to a machine learning process. During the machine learning process, labeled training data is provided as an input to neural network model 160, and the values of trained model parameters 164 are iteratively adjusted until the predictions generated by neural network 160 match the corresponding labels with a desired level of accuracy.

For improved performance, processor 130 may execute neural network model 160 using a graphical processing unit, a tensor processing unit, an application-specific integrated circuit, or the like.

Device 103 may be communicatively coupled to a database 170 or another suitable repository of digital information. For example, database 170 may be configured as a structured database with contents organized according to a schema or other logical relationships (e.g., relational database). In some embodiments database 170 may be configured as a non-relational database, a semi-structured database, an unstructured database, a key-value store, or the like. Although database 170 is depicted as being coupled directly to device 103, it is to be understood that a variety of other arrangements are possible. For example, database 170 may be stored in memory 140, accessed via network 110, or the like.

Figure 2:
FIG. 2 is a simplified diagram of a data flow for information retrieval to some embodiments.

FIG. 2 is a simplified diagram of a data flow 200 for information retrieval to some embodiments. In some embodiments consistent with FIG. 1, data flow 200 may be implemented using various components and/or features of system 100, as further described below.

As depicted in FIG. 2, an application 202 is communicatively coupled to an information retrieval system 204. In some embodiments consistent with FIG. 1, information retrieval system 204 may correspond to information retrieval program 150. Application 202 generally corresponds to a program that is configured to provide queries to information retrieval system 204 and handle responses from information retrieval program 204. For example, application 202 may correspond to a web application or a mobile application that receives queries from a user, sends the queries to information retrieval system 204 (e.g., via an API), and receives and renders corresponding responses. In some embodiments consistent with FIG. 1, application 202 may include a front-end component that runs on device 104, a back-end component that runs on device 103, or the like. In some embodiments, information retrieval system 204 may provide a standardized API or other interface that allows information retrieval system 204 to communicate with various types or versions of applications. In some embodiments, information retrieval system 204 may provide a user interface that allows user to provide queries to information retrieval system 204 directly, bypassing application 202.

Information retrieval system 204 includes a plurality of modules 210-250 that are used to fulfill the user's request. In some embodiments, modules 210-250 may each be components of an integrated program. In some embodiments, modules 210-250 may be independent programs (e.g., microservices) that operate independently of one another and communicate with each other via standard interfaces. Information retrieval system 204 can be distributed. For increased performance and parallelism, information retrieval system 204 may include multiple instances of modules 210-250.

A controller module 210 of information retrieval system 204 receives and handles queries (and/or other types of requests) from application 202. Controller module 210 is coupled to one or more other modules of information retrieval program 204 (e.g., modules 220-250) and coordinates among the other modules to fulfill the request. In some embodiments, the process of fulfilling the request may vary depending on the type of the request.

A knowledge base module 220 of information retrieval system 204 provides access to a knowledge base that identifies various types of relationships among information. For example, knowledge base module 220 may store collections of terms that are known to share a given relationship (e.g., the terms may be synonyms of one another). In some embodiments, the information and their associated relationships may be stored and retrieved using a knowledge graph or other suitable data storage techniques.

In general, it is desirable for the knowledge base stored by knowledge base module 220 to be comprehensive with respect to the subject matter of interest. A comprehensive set of relationships may be identified and aggregated using a variety of techniques. In some embodiments, the knowledge base may be built by starting with an existing knowledge base, such as the Unified Medical Language System (UMLS) in the case of the biomedical domain, and then aggregating onto it other sources of domain-specific information. For example, data may be aggregated from external databases (e.g., publicly available databases and proprietary or customer-specific databases). Relationships among the aggregated data may be identified using a neural network model (e.g., neural network model 160) or other information retrieval methods configured to mine relationships from the aggregated data.

A search module 230 of information retrieval system 204 provides a search engine capable of searching a corpus of text (e.g., a collection of documents, database records, and/or the like) based on a query term. In some embodiments, search module 230 may identify and retrieve complete text documents or database records from the corpus that are determined to be relevant to the query term. However, as discussed previously, this approach has various limitations. For example, when the user is seeking to make a determination or inference based on aggregated information (e.g., to determine of whether a particular drug has been shown to be effective against a particular disease based on an aggregate of studies performed on the drug), search results that simply include a list of relevant documents may not clearly and directly respond to the user's query. This approach may therefore entail tedious and time-consuming efforts on the part of the user to examine each of the search results to piece together the desired information and make a suitable determination or inference.

To address these limitations, search module 230 may be configured to return a list of text fragments that match the query term, rather than (or in addition to) a list of matching documents or records. This fragment-based search approach yields localized portions of documents (e.g., a few words, sentences, or paragraphs) that contain information of interest, e.g., information that is directly relevant to the determination or inference that the user is seeking to make. In this manner, where a document is not generally relevant to the user's query but contains a responsive fragment, the responsive text fragment is returned in the search results even if the document as a whole would not be relevant enough to be included in a list of matching documents. Conversely, where a document strongly matches the query term but does not include any fragments that directly respond to the query, the document may not yield any fragments in the list of matching text fragments. Moreover, if a given document or record includes more than one matching text fragment, the single document or record may yield multiple entries in the returned list of text fragments. As a result, the fragment-based search approach may improve the overall the relevance and completeness of the search results. Illustrative embodiments of a fragment search module are described in further detail below with reference to FIG. 3.

A statistical analysis module 240 of information retrieval system 204 provides tools to statistically analyze information from other modules of information retrieval system 204, such as the list of search results provided by search module 230. A wide range of statistical analyses may be performed, depending on factors such as the type of request received from the user. For example, statistical analysis module 240 may compute the statistical significance of various entities and terms appearing in the list of search results from search module 230 (e.g., a count of the number of occurrences of a given term in the search results, a count of the number of co-occurrences of the term with other terms, a score or ranking to compare the significance of a term relative to other terms, or the like). In performing the statistical analyses, statistical analysis module 240 may communicate with and retrieve information from other modules of information retrieval system 204. Examples of statistical significance metrics that may be computed using statistical analysis module 240 are described in further detail below with reference to FIG. 4.

A machine learning module 250 of information retrieval system 204 provides tools for applying machine learning models (e.g., neural network model 160) to information from other modules of information retrieval system 204, such as the list of search results provided by search module 230. In some embodiments, machine learning module 250 may include a natural language processing (NLP) pipeline for analyzing the text of the search results. The NLP pipeline may include NLP primitives (e.g., tokenization, embedding, named entity recognition, etc.). Moreover, the NLP pipeline may include pre-trained rule-based or machine learning models, including but not limited to negative expression finders, sentiment classifiers, entity extractors, or the like. Further statistical analysis may be performed on the output of the NLP pipeline to identify relationships and associations among the results.

In some embodiments, machine learning module 250 may be associated with a subsystem, such as a GPU cluster, that hosts a set of biomedical and clinical relationship machine learning models. The set of machine learning models may be continuously updated for improved accuracy. These models may be available to other modules of information retrieval system 204 for obtaining accurate inferences on large numbers of sentences (or other suitable text fragments) relevant to user queries.

An inference database module 260 of information retrieval system 204 may optionally be provided to store pre-computed inferences made by the machine learning modules of machine learning module 250. For example, inference database module 260 may include a high performance database that enables efficient retrieval of pre-computed inferences at run-time during a user query. In such embodiments, machine learning module 250 may be bypassed at run-time. In some embodiments, inference database module 260 may include inferences made by each machine learning model of machine learning module 250 for each text fragment or patient note with contents relevant to that model.

Data flow 200 may correspond to an instance of a "base platform" that can be run within the confines of an individual organization or hospital's patient clinical data repository. The framework can also be applied to a federation of compatible base platforms, each one operating within an individual hospital or institution's patient clinical data system. The individual hospital/information systems may not share information other than using a federated, privacy-preserving information retrieval protocol that enables the aggregation of clinical and biomedical information from across all the individual base platforms. Such a federated protocol can also potentially enhance an existing patient information sharing protocol, such as FHIR (Fast Healthcare Interoperability Resources).

Figure 3:
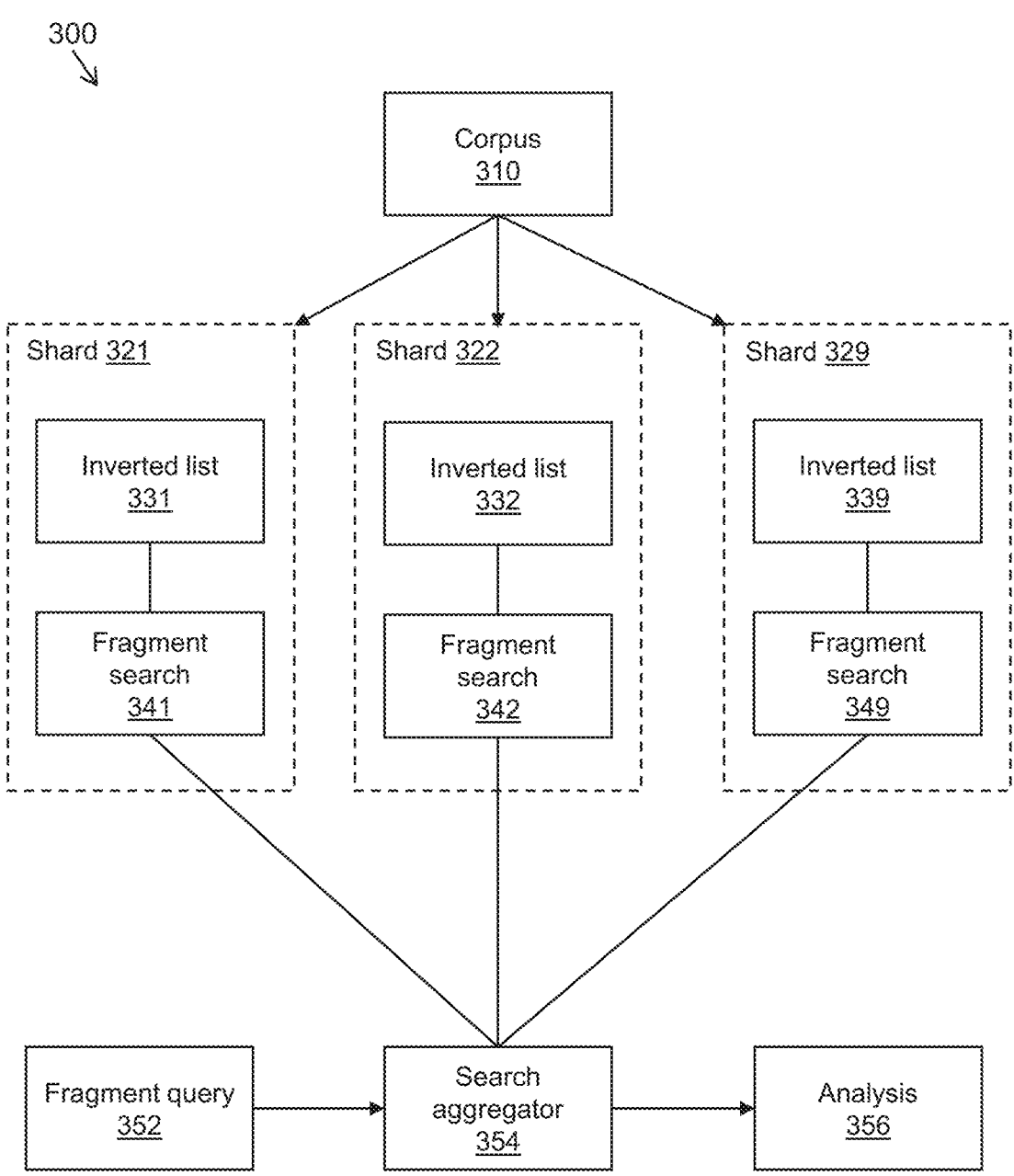
FIG. 3 is a simplified diagram of a data flow for fragment searching according to some embodiments.

FIG. 3 is a simplified diagram of a data flow 300 for fragment searching according to some embodiments. In some embodiments consistent with FIG. 2, data flow 300 may be implemented using search module 230.

A corpus 310 corresponds to a collection of text, such as a collection of one or more text documents or database records. For example, corpus 210 may correspond to documents 121-129 received from devices 101-109 and/or may include documents stored locally by device 103. In some embodiments, corpus 310 may be stored in memory 140, database 170, in an on-chip memory (e.g., cache), or the like. The documents in corpus 310 can be stored in a native format (e.g., in the format as received from devices 101-109), or various pre-processing operations may be performed on the received documents to modify the content or format of the documents. For example, non-text data (e.g., image data) and/or metadata may be removed from the documents, text data may be extracted from the documents (e.g., by optical character recognition), or the like. The format of the documents may be converted to a uniform format, or data from the documents may be used to populate a database (e.g., database 170). In some embodiments, corpus 310 may be dynamically updated.

The contents of corpus 310 can relate to general subject matter (e.g., a collection of news articles or Wikipedia entries covering a variety of topics) or domain-specific subject matter. Illustratively, corpus 310 may relate to biomedical subject matter. For example, corpus 310 may include text from journal articles, reference textbooks, patent applications, websites, etc. related to biomedical fields. In some embodiments, corpus 310 may include patient clinical data. Corpus 310 can be drawn from a wide variety of sources, such as molecular databases, scientific literature, insurance documents, pharmaceutical company websites, news feeds, regulatory information (clinical trials, SEC filings, IP), clinical data systems associated with hospitals or other institutions, or the like.

As depicted in FIG. 3, corpus 310 is partitioned into a plurality of subsets. Each subset may be provided to a respective shard among shards 321-329. In some embodiments, splitting corpus 310 among shards 321-329 may facilitate processing of corpus 310 using distributed computing resources (e.g., using distributed processors and/or storage systems). For example, one or more of shards 321-329 may be located on different machines within a data center and/or in different data centers. In some embodiments, each of the subsets of corpus 310 may be approximately equal in size, e.g., they may occupy similar total disk space or they may include a similar number of documents.

Each of shards 321-329 includes a corresponding inverted list 331-339. Each of inverted lists 331-339 identifies, for each token (e.g., word) in the corresponding subset of corpus 310, a list of occurrences of the token within the subset of corpus 310. For example, an inverted list 331-339 may identify the positions of each occurrence of the token within the subset of corpus 310 (e.g., the positions within a contiguous array of text that corresponds to a concatenation of each document in the subset of corpus 310). In some embodiments, the inverted list 331-339 may identify a document identifier corresponding to the document in which the token occurs, an offset within the document to the occurrence of the token, or the like. In some embodiments, each entry in the inverted list 331-339 may include a plurality of location identifiers for each occurrence of each token. The plurality of identifiers may be stored in an appropriate data structure, such as a triplet that identifies (1) the array index of the occurrence of the token within a contiguous array of concatenated documents, (2) the document identifier of the occurrence, and (3) the offset within the identified document to the occurrence.

In some embodiments, the inverted lists 331-339 may be ordered to facilitate efficient lookup of tokens. For example, the inverted lists 331-339 may be ordered based on an ascending order of each token's positions within the array of text corresponding to the subset of corpus 310. The inverted list 331-339 may be indexed using integer values associated with each token, such that given an integer corresponding to a token, the data structure containing inverted list 331-339 efficiently returns a corresponding list of occurrences of the token.

Each of shards 321-329 further includes a corresponding fragment search module 341-349. Each of fragment search modules 341-349 is configured to receive a fragment query 352 and generate a response to the fragment query by accessing data from inverted lists 331-339. A fragment query 352 may be distributed to the fragment search modules 341-349 using a search aggregator 354. The search aggregator 354 may then receive and aggregate the search results generated by fragment search modules 341-349. The search results may then be used for subsequent analysis 356. For example, in some embodiments consistent with FIG. 2, the analysis 356 may be performed using one or more of knowledge base 220, statistical analysis module 240, or machine learning module 250.

In some embodiments, fragment query 352 includes one or more query parameters indicating the desired search criteria for the fragment search. For example, fragment query 352 may include a query parameter (e.g., a combination of one or more tokens, words, or multi-word phrases to be searched, optionally joined by Boolean operators, such as AND, OR, and NOT). Fragment query 352 may also include a size parameter indicating the desired size of the text fragment returned by fragment search module 341-349. Fragment query 352 may further include a document parameter that specifies one or more criteria that a document should satisfy as a prerequisite for fragments in the document to be included in the search results. For example, the document parameter may include a criteria that eligible documents include a specified single or multi-word phrase (or logical combinations thereof) or a criteria that eligible documents be associated with document metadata (e.g., author names, publication years, document source, document type, or the like). Consistent with such embodiments, fragment query 352 may be represented using an appropriate data structure for transmitting and processing the various search parameters, such as a data structure represented as <FragQuery, FragmentSize, DocumentSpecifier>, where FragQuery denotes a query parameter, FragmentSize denotes a size parameter, and DocumentSpecifier denotes eligibility conditions for documents to be included in the search results.

FIG. 4 is a simplified diagram of a method 400 for retrieving clinical information based on clinical patient data according to some embodiments. According to some embodiments consistent with FIGS. 1-3, method 400 may be performed by processor 130 during the execution of information retrieval program 150. For example, method 400 may be performed using controller module 210.

At an optional process 410, specifications for one or more patient cohorts (or study groups) are received by a controller (e.g., controller module 210). The specifications can include a variety of parameters for identifying a group of patients, such as demographics (e.g., age, race, gender, and the like), diagnoses, drugs, treatment plans, timeframes, and the like, and combinations thereof. Based on these specifications, the controller may create a cohort of patients by applying suitable filters on the patient data records that are used for subsequent processes of method 400. The filter may be applied at any suitable point during method 400.

When one or more patient cohorts are specified at optional process 410, then subsequent processes of method 400 may operate on clinical data records associated with these cohorts. Otherwise, the subsequent processes may be applied to a default set (e.g., all) of the clinical data records.

At a process 420, a query is received by a controller (e.g., controller module 210). The query can include one or multiple tokens (e.g., words, sentences, etc.), Boolean operators, constraints, filters, and various other parameters. In some embodiments, the query may be included in a request sent by an application, such as application 202. Consistent with such embodiments, the request may be received via and API. In response to receiving the request, the controller may process and respond to the request by gathering information responsive to the query according to one or more of the following processes 420-450. In distributed computing environments, the information may be gathered via communications transmitted to and from various modules located at different network nodes. In some embodiments, the query may include information that identifies one or more types of statistical analysis or machine learning inferences to perform on the clinical data records. These analyses and inferences may be identified explicitly in the query or may be determined based on information associated with the query (e.g., the type of query, terms included in the query, or the like).

Specifying a cohort at process 410 and receiving a query to be applied to the cohort at process 420 provides a powerful and flexible process for extracting insights from clinical data records. For example, once a cohort is specified, the practitioner may want to pose several kinds of queries, described below, with respect to the patients in the cohort based on patient data, often contrasting with another of cohort patients (a 'control' group). Patient treatments may be past or ongoing.

An illustrative example of a cohort is patients from a particular demographic who were administered a particular drug X. The practitioner may want to know the overall distribution of diseases that set of patients were afflicted with anytime over the patient's timeline. Alternatively, the practitioner may want to know the overall distribution of diseases the patient was afflicted with during a specific temporal vicinity of the drug X being administered to the patient.

On the same cohort as above, another type of question that a practitioner may be interested in is the following: What specific disease conditions afflicting the patient did the physician deem as an indication that drug X could cure or mitigate in the patient, and for how many patients was this the case? What specific disease conditions afflicting the patient did the physician deem an adverse side effect attributable to drug X being administered to the patient, and for how many patients was this the case?

For the same cohort, the practitioner may additionally or alternately want to know the indications and adverse effects for some other drug Y in that cohort, along with patient numbers.

The following are further illustrative examples of cohorts and queries that may be addressed using method 400:

First, consider a cohort of patients who have a particular diagnosis code and a specific range of values on a lab test. Diagnosis codes are meant to cover diseases that patient could potentially be afflicted with, but they generally provide incomplete coverage. Moreover, diagnosis codes are often noisy and ambiguous. Accordingly, for this type of cohort a practitioner may want to know one or more of the following: What is the distribution of specific diseases that that set of patients is actually afflicted with? What is the distribution of specific medications that that set of patients was administered? What is the distribution of comorbidities observed afflicting patients suffering from disease Y and who were administered drug X?

Moreover, consider a cohort of patients administered drug X for disease condition Y. For this cohort, a practitioner may want to know one or more of the following: what is the fraction having positive outcomes. Is there a pattern whereby ethnicity or age or gender or affluence or some combination has distinctly better or worse outcomes?

Furthermore, consider two distinct interventions X and Y for the same disease condition D—during treatment which intervention has better standard of life for patients, when X and Y are compared? What kinds of side effects are observed for X relative to Y? Are there any comorbidities of D that seem to determine the physician's decision to use X and Y?

Consider a new clinical trial being pursued by a pharma company. In general, each clinical trial has distinct inclusion and exclusion criteria. What set of patients optimally matches the criteria from among the patient set available?

What diagnosis code, medication, procedures and lab tests found in structured data are best predictors from within structured data for patients afflicted with NSCLC? In practice, structured data such as diagnosis codes, medication, procedures and lab test measurements are more easily avail-able subsets of clinical data for pharmaceutical companies than unstructured text data. As a result, pharmaceutical companies may estimate the size of NSCLC afflicted patient set from incomplete ambiguous and noisy structured data. However as mentioned before NSCLC, like several other disease conditions, does not have a specific diagnosis code in the ICD10 family of diagnosis codes. Typically, the ICD code given to NSCLC maps to a broader category—e.g. lung cancer. Accordingly, an NSCLC classification may be based on other structured data attributes. In such situations unstructured text data can be used to build ground truth data sets for building a classifier which then can be used on structured data.

What patients coded with the diagnosis code for Multiple Sclerosis actually are patients afflicted with a different disease Neuromyelitis optica, which has similar symptoms but is a different disease mechanism. Again, this situation arises when there is incomplete, ambiguous, or noisy structured data; so that the ground truth for a classifier may be built using unstructured text.

At a process 430, the query is optionally expanded to include one or more related terms. The related terms may be retrieved from a knowledge base, such as the knowledge base of knowledge base module 220. In some embodiments, the related terms may share a predetermined relationship with the terms in the original query (e.g., the terms may be synonyms of one another). In this manner, retrieving the related terms may broaden the query to include terms with similar meanings to the terms provided by the user.

At a process 440, a list of search results is retrieved based on the expanded query (or the original query when process 430 is omitted). The list of search results includes documents or passages (or information that identifies such documents or passages) that match the query. The list of search results may be retrieved via a search engine or search module, such as search module 230. In some embodiments, the search results may be retrieved from a corpus of text (e.g., a collection of documents, database records, and/or the like) based on a query term provided by the controller. For example, the search results may correspond to the results of a fragment-based search. In this approach, the search results include fragments (e.g., a few words, sentences, paragraphs, or other localized portions of documents) that contain information of interest. Illustrative embodiments of a fragment-based search are discussed in further detail below with reference to FIG. 5. In some embodiment, each element in the list of search results may include at least a portion of a clinical data record associated with a patient in the patient cohort specified at process 410.

In some embodiments, the list of search results may be referred to as a "context" of the query and may be stored or indexed using a suitable data structure. The context includes windows of the corpus that include query terms, along with terms that appear near the matching query term within the corpus (e.g., terms that appear within a window size of n tokens of the matching query term in the corpus). More generally, a "context" can include documents or other sets of text from the corpus that are relevant to the information retrieval task, whether determined based on a query, manually curated, or determined based on other criteria, shared attributes, or the like. For example, the context can include a set of documents corresponding to "'biomedical news articles encountered this week." Such contexts can be analyzed using method 400 (as further discussed below in a similar manner to a context based on a query.

In some embodiments, the context may include one or more types of contexts, e.g., (a) a context based on a query generated using processes 420-440, (b) a context based on a set of documents that have shared attributes or (c) a combination thereof. For clinical data information retrieval applications, the context may include a collection of patient records (e.g., patient notes, reports, narratives, etc.). The patient records in the context may have one or more shared attributes or may include a query term or its synonyms. For example, the patient records may include: health records for a particular patient; health records for a plurality of patients that include a particular term (e.g., NSCLC) or its synonyms; ECG reports for patients whose records include the term "pulmonary hypertension," or the like. Such a context may be based on the specification of the patient cohort received at process 410, the query terms received and processed at processes 420-440, or a combination thereof.

The context may be binary or nonbinary. In a binary context, terms in the corpus are either included in the context (e.g., if they are within n tokens of an appearance of the query term) or they are omitted from the context. In a non-binary or "smooth" context, terms in the corpus may be weighted (e.g., assigned a value between 0 and 1) based on factors such as the distance from the query term. For example, the weight assigned to a term in a non-binary context may attenuate exponentially based on distance of the term from the query term.

At a process 450, one or more entities are optionally identified within the list of search results. For example, in the context of biomedical applications, illustrative examples of entities may include names of drugs, diseases, genes, pharmaceutical companies, research institutions, or the like. In some embodiments, the one or more entities may be identified by referencing a knowledge base, such as the knowledge base of knowledge base module 220. For example, the knowledge base may store collections of entities, such that the list of search results may be compared to the collections of entities to identify entities in the list of search results. In some embodiments, natural language processing techniques, such as named entity recognition, may be used to accurately identify entities in the list of search results. In some embodiments, the entities within the list of search results may be pre-identified (e.g., using a machine learning model configured to perform named entity recognition) and stored in a database, such as inference database module 260. Accordingly, identifying the one or more entities may include retrieving the pre-identified entities from the database for each item in the list of search results.

At a process 460, one or more inferences are computed for each item in the list of search results. In some embodiments, the inference may correspond to the output of a machine learning model that identifies a relevant sentiment or association for a given text input. For example, a sentiment model may identify whether a given sequence of text indicates that a drug was (positive sentiment) or was not (negative sentiment) effective. An example of an association model is one that indicates whether a particular drug was administered to treat a particular disease (this is an example of a drug-disease "indication association"). Another example is whether that disease was deemed to be an adverse side-effect of consuming that drug (this is an example of a drug-disease "adverse effect association"). In some embodiments, the inferences may be pre-computed and stored in a database, such as inference database module 260. Accordingly, computing the one or more entities may include retrieving the pre-computed inferences from the database for each item in the list of search results. In some embodiments, one of more of the machine learning models may be associated with metadata or other information that is used to determine whether a particular machine learning model is relevant to a particular query. Accordingly, the one or more inferences computed at process 460 include those inferences that are likely to yield relevant insights for responding to the present query. Other inferences that are determined not to be relevant may not be computed, resulting in more efficient use of computational resources.

At a process 470, an aggregate statistical analysis is provided based on the one or more inferences. The statistical analysis may be performed by a statistical analysis module, such as statistical analysis module 240, by a machine learning module, such as machine learning module 250, or by a combination of modules. The statistical analysis may include aggregating or grouping the search results based on the one or more inferences for each item in the list of search results.

At process 480, a response is provided that includes the aggregate statistical analysis. In some embodiments, the response may be transmitted to an application, such as application 202, and displayed to a user. The response may provide interactive user interface elements to the user to allow the user to interact with the search results or the enriched sets. For example, for the items in the enriched sets, the user may hover over the items to view the statistical analysis (e.g., the significance scores, the relationship scores, or the like) associated with the items.

FIG. 5 is a simplified diagram of a method 500 for performing a fragment search according to some embodiments. In some embodiments consistent with FIGS. 1-4, method 500 may be performed by a search module, such as search module 230. The fragment search results generated using method 500 may then be retrieved by a controller at process 430 of method 400.

At a process 510, a corpus, such as corpus 310, is partitioned into a plurality of subsets. The corpus includes a plurality of text documents or database records. In some embodiments, each of the subsets of the corpus may be approximately equal in size, e.g., they may occupy similar total disk space or they may include a similar number of documents.

At a process 520, each of the plurality of subsets are distributed to a corresponding plurality of shards, such as shards 321-329. In some embodiments, splitting the corpus among the shards may facilitate processing of the corpus using distributed computing resources (e.g., using distributed processors and/or storage systems). For example, one or more of the shards may be located on different machines within a data center and/or in different data centers.

At a process 530, for each shard, the one or more documents in the respective subset of the corpus are concatenated to form a text array. For example, the text array may be contiguous with respect to the one or more documents.

At a process 540, for each shard, an inverted list is generated. The inverted list includes an entry for each token (e.g., vocabulary word), in the corpus. Each entry includes a list of occurrences of the token in the corpus. For example, the list of occurrences may identify the positions of each occurrence of the token within the array formed at process 530. In some embodiments, the inverted list may include a document identifier corresponding to the document in which the token occurs, an offset within the document to the occurrence of the token, or the like. In some embodiments, each entry in the inverted list may include a plurality of location identifiers for each occurrence of each token. The plurality of identifiers may be stored in an appropriate data structure, such as a triplet that identifies (1) the array index of the occurrence of the token within a contiguous array of concatenated documents, (2) the document identifier of the occurrence, and (3) the offset within the identified document to the occurrence.

The inverted list may be ordered to facilitate efficient lookup of tokens. For example, the inverted list may be ordered based on an ascending order of each token's positions within the array of text. The inverted list may be indexed using integer values associated with each token, such that given an integer corresponding to a token, the data structure containing inverted list efficiently returns a corresponding list of occurrences of the token.

At a process 550, a fragment query, such as fragment query 352, is received by a search aggregator, such as search aggregator 354. The fragment query includes one or more query parameters indicating the desired search criteria for the fragment search. For example, the fragment query may include a query parameter (e.g., a combination of one or more tokens, words, or multi-word phrases to be searched, optionally joined by Boolean operators, such as AND, OR, and NOT). The fragment query may also include a size parameter indicating the desired size of the text fragments in the search results. The fragment query may further include a document parameter that specifies one or more criteria that a document should satisfy as a prerequisite for fragments in the document to be included in the search results. For example, the document parameter may include a criteria that eligible documents include a specified single or multi-word phrase (or logical combinations thereof) or a criteria that eligible documents be associated with document metadata (e.g., author names, publication years, document source, document type, or the like).

At a process 560, the fragment query is distributed to the plurality of shards. Upon receiving the fragment query, each of the plurality of shards performs a lookup on the respective inverted list to identify matching fragments, yielding a set of fragment search results. In some embodiments, search criteria included in the fragment query (e.g., a restriction on the eligible documents to be included in the search) may be applied during the lookup.

At a process 570, the sets of fragment search results from the plurality of shards are aggregated by the search aggregator. For example, the search results may be compiled, concatenated, sorted, ranked, or the like. Upon aggregating the search results, the search results may be provided to a controller or another module for further analysis, or may be returned to a user.

FIG. 6 is a simplified diagram of a data table 600 storing patient clinical data according to some embodiments. In some embodiments consistent with FIGS. 1-5, data table 600 may correspond to at least a part of a corpus of patient clinical data, such as corpus 310, and may be stored in a database, such as database 170.

Data table 600 generally corresponds to patient clinical data for a single patient. A clinical patient database with data from a plurality of patients may include one or more such data tables (or may utilize any other suitable data structure or combination of data structures).

Each of rows 611-619 is time stamped and represents a single time unit (e.g., days or weeks or months, for example) in which one or more patient data elements occurred in the patient timeline. Each of columns 621-669 represents one patient data element. The patient data elements shown in FIG. 6 are illustrative, and various embodiments may include more, fewer, or different patient data elements and the patient data elements may be arranged differently than shown.

In the illustrative embodiment of FIG. 6, the first two columns 621 and 622 represent unstructured text documents pertaining to the patient. A document may be a physician's narrative on the patient's health including and up to the present moment: it may describe the patient's health, diagnosis, prescribed medications or interventions, their effects etc., as also family and social history of the patient all in unstructured text. Often the IT system in use at the hospital or institution may influence the headings or sections in which the physician narratives or other patient documents are organized. A document may also be a specialized report such as a report on an ECG or pathology slide or radiology image by a concerned specialist. A document may also be a hospital log with some minimal information logged by a nurse practitioner or a resident doctor. A document may also be fully or partially auto-generated by the hospital IT system using a pre-programmed knowledge base in response to medication or intervention codes coming from physician prescriptions. For example, the knowledge base may contain patient-agnostic information about the medication, how it should be consumed, stored, or the like; and possible side effects and known interactions with other medications or conditions, and so on.

The next set of columns 631-639 are data pertaining to laboratory tests and measurements the patient has been subjected to. The number of distinct tests available may be of the order of tens of thousands.

The next set of columns 641 and 642 includes the physician diagnoses for the patient's disease condition. These diagnoses may come from an enumerated set of possible diagnoses that may apply to any patient. Some hospitals or institutions may use standardized or non-standardaized sets of diagnoses and diagnosis codes, or a combination of standard and non-standards diagnoses and diagnosis codes. Columns 643-649 correspond to heuristic based data augmentation may be added to data table 600 based on a knowledge base (e.g., knowledge base 220), such as a knowledge graph built from public domain literature on diseases and diagnoses.

The next set of columns 651 and 652 includes drug and medication columns corresponding to the patient. Columns 651 and 652 may identify a drug or medication and may include dosage information as well as course start and end dates. Optional augmented data, such as standardized names for drugs computed from a knowledge base (e.g., knowledge base 220), may be provided in columns 653-659.

Other data elements in columns 661-669 may include a variety of other data associated with the patient. In some embodiments, columns 661-669 may store unstructured data, such as images (radiology, pathology), recordings (ECGs, Echos etc), time-series data, as well as related structured information.

In some embodiments, data table 600 may be sparsely populated. The number of columns are indicative of the variety of patient data elements that can constitute a patient timeline, but at any given time one or more of the columns may be empty.

Moreover, various elements stored in data table 600 may be ambiguous, noisy, or uncertain. This is particularly the case for structured data, such as diagnosis codes. For example, even though diagnoses and diagnosis codes ontologies, especially from standardized bodies, are intended in spirit to cover a wide range of conceivable diseases or conditions that a patient may have, in practice the ontologies are generally incomplete. As new disease mechanisms get discovered, newer and newer subcategories of diseases get named/specified in the discourse of physicians, research literature and clinical trials such that the diagnoses ontologies are often lagging behind. Consider for instance the fact that NSCLC, a fairly significant and specific form of lung cancer, does not at this time have a corresponding standardized ICD10 diagnosis code even though its existence has been known for years. Accordingly, identifying a set of patients with a particular disease that is not yet captured in an ontology is challenging.

In addition, distinct disease mechanisms often have similar symptoms and phenotypes. In this case, patients may be initially or partially or even completely misdiagnosed in their diagnosis code data, making inference of true disease difficult. One example (among many) of a pair of distinct diseases with similar phenotypes is Multiple Sclerosis (MS) and Neuromyelitis Optica (NMO). Here even if these have distinct diagnosis codes, often NMO patients get initially or completely misdiagnosed as MS patients, because MS is a more prevalent disease. Such noisiness is difficult to remedied using data curation or data augmentation techniques because of the patient-specific biology considerations.

Another source of ambiguity and uncertainty is that a patient journey may often involve stretches of his or her timeline in which he or she was being treated at some facility outside the current institution. The diagnoses, medications, lab tests, intervention and other information elements of such patients' timelines may then be missing in the current institution's clinical data system.

In comparison to structured clinical data, unstructured text data may generally be more complete and contain more information than the structured data. For example, unstructured physician notes may mention the precise disease name and sentiment much more precisely than diagnoses codes assigned to the patient. Also, an unstructured note gives the patient an opportunity to recount capture any outstation diagnosis, intervention or lab test he or she may have had. Naturally, the lack of structure enables free text notes to capture more information in physician narratives as well as reports from specialists—the ease arises both from natural language and because there are many clinical facets (for example, quality of care, intervention outcomes, interactions between comorbidities and medications) that do not have a designated structured data field in which they can be captured. Accordingly, the use of neural network models for processing text (e.g., the machine learning models of machine learning module 250) may make the extraction of clinical information from unstructured text more reliable than structured clinical data.

Time information (e.g., the time stamps in data table 600) may be used in various ways for different applications. Pharmacological and clinical research applications are typically concerned with how phenotypes and diseases and observed lab test measurements progress over an individual patient's timeline, interacting with and responding to interventions. In such application contexts, the "calendar time" at which a patient data event occurs may be inconsequential— as a result, two patients whose calendar timelines don't have an overlap but whose medical trajectories bear similarities may still be part of the same retrospective study group data set. However, there are also epidemiological research applications studying areas like the current Covid19 pandemic, or seasonal onsets of diseases or phenotypes caused by environmental or other events at some fixed point of time where lining up and analyzing patient data based on their absolute calendar times becomes relevant.

Figure 7A:
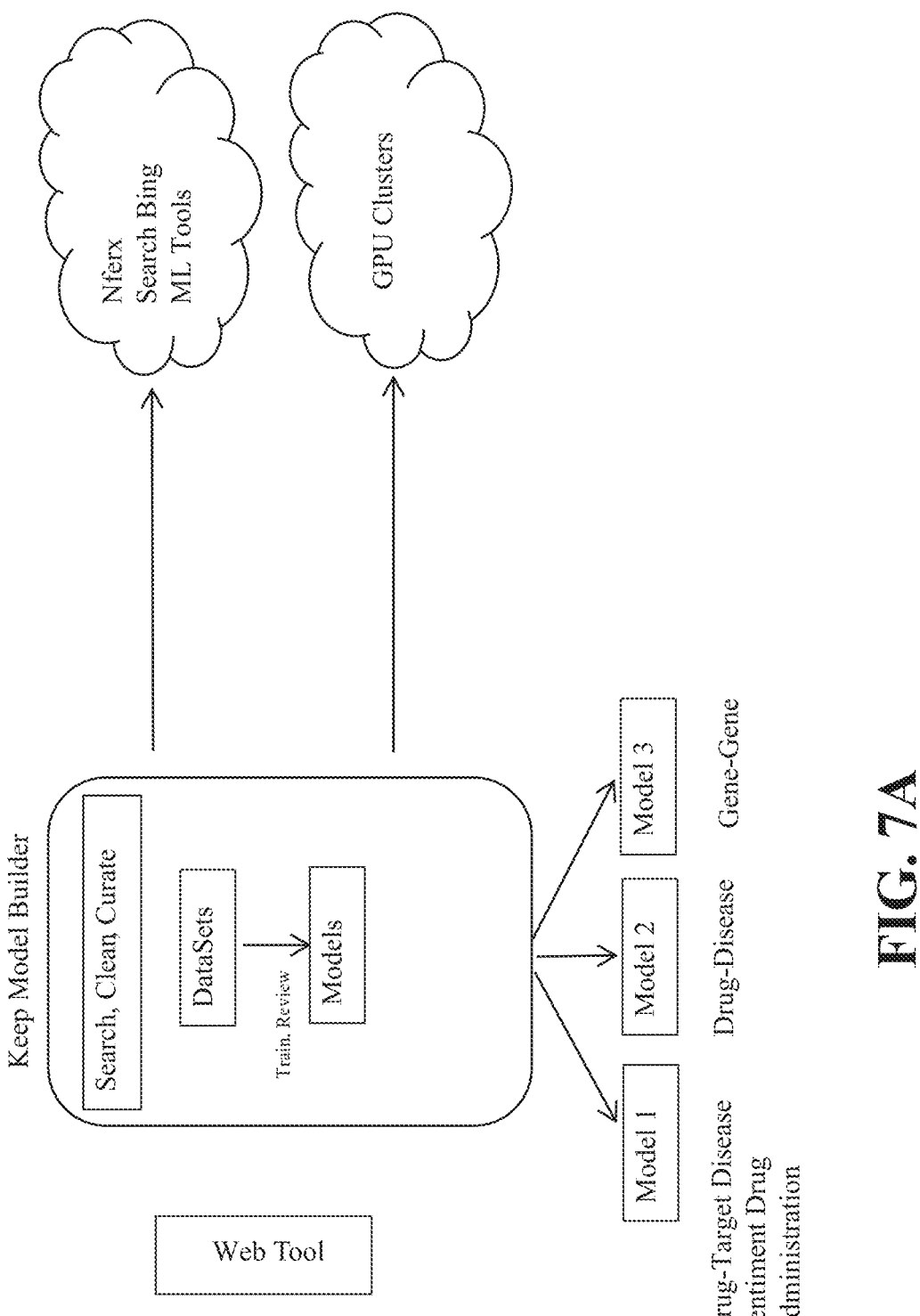

FIGS. 7A and 7B are simplified diagrams of a machine learning model (e.g., a deep model) builder application 700 according to some embodiments. The machine learning model builder application 700 may provide a cloud-based environment for users (e.g., scientists) to build, train, review, and improve the performance of machine learning models, such as the sentiment and association machine learning models used in method 400. For example, the three illustrative models depicted in FIG. 7 identify associations between a drug and a target, a drug and a disease, and a pair of genes, respectively. The machine learning model application 700 may provide capabilities for the user to generate data sets used in the model building process, such as training, testing, and validation data sets. Creating the data sets may include searching for relevant data, cleaning, and curating the data sets. Based on these data sets, the models may be trained, e.g., using supervised or semi-supervised training methods. In some embodiments, the models built using machine learning model building application 700 may added to a model repository (e.g., machine learning module 250). Similarly, existing models within the model repository may be improved using the machine learning model builder application 700.

Figure 8B:
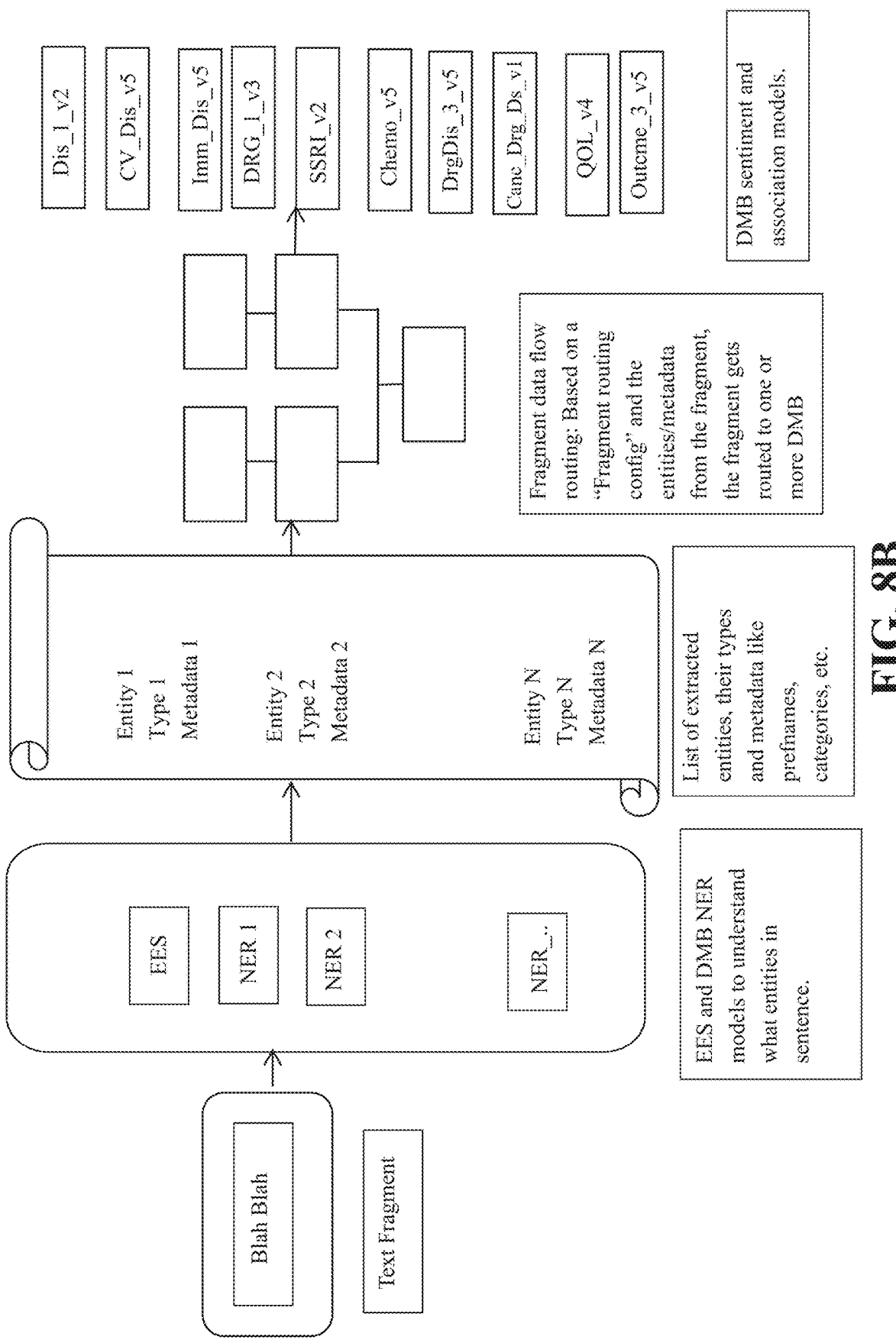

FIGS. 8A and 8B are simplified diagrams of a data flow 800 for populating an inference database, such as inference database module 260, according to some embodiments. As discussed previously, a machine learning module, such as machine learning module 250, may be configured to execute one or more machine learning modules that perform a variety of tasks, including named entity recognition (NER), classification, sentiment analysis, and association analysis. In embodiments consistent with FIG. 7, these models may be built or improved using machine learning model builder application 700, or may be otherwise provided. As depicted in FIG. 8A, the machine learning module includes a GPU cluster that is loaded with models from a repository. The machine learning module receives input data and stores the resulting output data in the inference database. The outputs may be aggregated, e.g., by document, patient, or the like. For example, aggregation of the outputs may enable faster lookup and response time than storing outputs for individual text fragments. As discussed previously, one or more of the machine learning models may include metadata that may be used to determine whether the model is relevant to a particular text fragment. Accordingly, when populating or updating the inference database, inferences may be provided for those models with metadata that match a given text fragment. By contrast, in embodiments that do not use the optional pre-computed inference database, inferences may be computed in a just-in-time approach, and metadata matching may be performed in real-time while computing the response for a user-query. In such embodiments, caching techniques may be used to reduce the computational load associated with computing real-time inferences.

Illustratively, the input data includes unstructured text data broken into sentences. As shown in FIG. 8A, the input data comes from patient data records and biomedical corpora, although other input data may be used. As shown in FIG. 8B, the text fragments (e.g., sentences) may be processed using one or more models arranged sequentially. Routing logic may be used to determine which models or sequences of models to include in the data flow. For example, one or more named entity recognition models may identify entities within a text fragment (which may include associated metadata). Based on those entities, the routing logic may select one or more sentiment or association models to run on the text fragment. In some embodiments, the inference database may be continuously updated as new (or improved) input data and models become available. As a result, the inference database may contain up-to-date inferences that can be retrieved with high performance in real-time.

Figure 9:
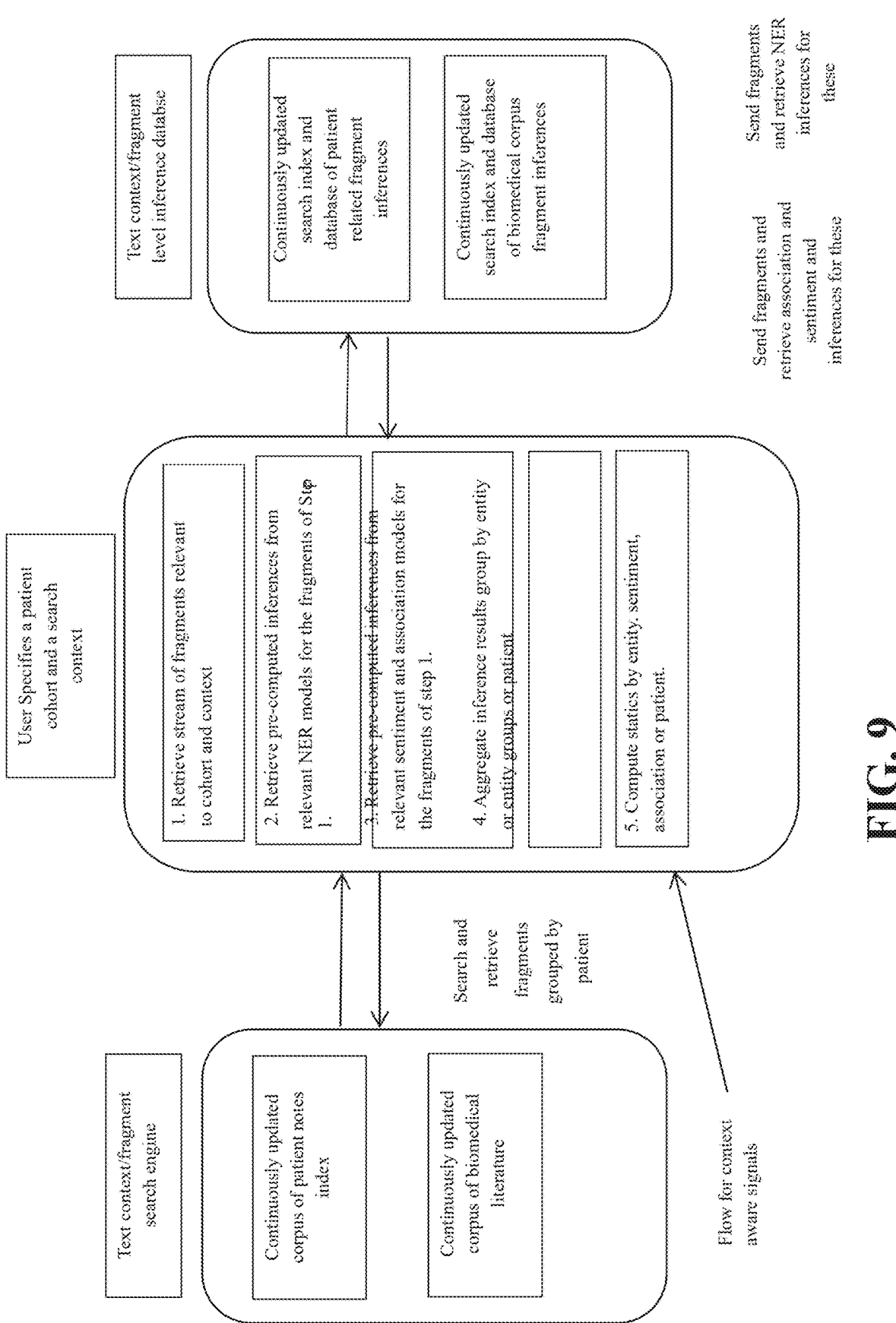
FIG. 9 is a simplified diagram of a data flow for retrieving clinical information based on clinical patient data according to some embodiments.

FIG. 9 is a simplified diagram of a data flow 900 for retrieving clinical information based on clinical patient data according to some embodiments. In some embodiments, data flow 900 may depict the flow of information during method 400, as described above.

FIG. 10 is a simplified diagram of a system 1000 for cohort analysis according to some embodiments. In some embodiments consistent with FIGS. 1-9, system 1000 may be implemented using various components and/or features of system 100 and data flow 200, as further described below.

For illustrative purposes, system 1000 is depicted in FIG. 10 as a layered architecture, although it is readily appreciated that other architectures are possible. A first layer 1010 includes one or more systems or applications that obtain and store clinical data and make the data available to one or more other layers of system 1000. In some embodiments, the applications of layer 1010 may obtain clinical patient data from a variety of information systems, including those associated with hospitals and other institutions. For example, the applications may be configured to continuously crawl such information sources for new or updated clinical data. The data is then loaded into a suitable data structure for subsequent retrieval, such as one or more databases. Examples of clinical data that is obtained using layer 1010 may include patient notes, ECG data, diagnosis records, medical information records, and the likes. Each data element for a given patient may be accessible using a patient identifier, and may be timestamped. In some embodiments consistent with FIG. 6, the clinical patient data may be stored in a data table, such as data table 600.

A second layer 1020 includes one or more systems or applications that analyze clinical patient data using, for example, artificial intelligence, machine learning, or statistical inference models. These models may be executed continuously as new or updated patient clinical data is made available by the first layer 1010. The model outputs may be stored and made available to other layers of system 1000. The models may illustratively be characterized as low level models that directly process the text, images, time-series data, and other types of patient clinical data made available at layer 1010; or as high level models that operate on the outputs of one or more lower level models (in addition to other information, as appropriate) to provide patient-level inferences. However, it is to be understood that these characterizations are illustrative and that other types of models may be used. In some embodiments consistent with FIGS. 2, 7A and 7B, the models of layer 1020 may include models that are made available by machine learning module 250 and may be developed using model builder application 700.

A third layer 1030 includes one or more systems or applications that are used to retrieve information based on user queries. In some embodiments, layer 1030 may include modules such as a biomedical knowledge graph (e.g., knowledge base module 220) that helps in the interpretation and enhancement of user queries as described previously, text indexing applications for retrieval of text fragments (e.g., sentences or paragraphs) or complete documents, information retrieval applications, or the like. Indexing applications may include temporal indexing around pre-determined events for retrieval of images and other clinical and genomic data. In some embodiments consistent with FIGS. 8 and 9, layer 1030 may include modules that implement one or more of data flow 800 or 900, e.g., to facilitate populating and retrieving information from an inference database.

A fourth layer 1040 includes systems or applications that interface with the other layers of system 1000 to handle a user query. For example, layer 1040 may include logic and associated frameworks that are configured to analyze the user query, determine the type of response the user is seeking (e.g., the patient cohorts, data enrichments, and statistical analyses that are relevant to the user query), and generate a response to the user query based on information obtained from the other layers of system 1000.

FIG. 11 is a simplified diagram of an information retrieval system 1100 implementing a federated protocol according to some embodiments. A plurality of different institutions 1111-1119 (e.g., hospitals, research institutions, universities, or the like) each implement a different cohort analysis system, such as system 1000. In general, each of the cohort analysis systems is configured to process clinical data from patient groups associated with a particular institution. Using a federated protocol to communicate with each of institutions 1111-1119, a federated engine front-end 1120 may be configured to perform cohort analysis and comparisons across patient groups from each of institutions 1111-1119. The federated protocol may preserve privacy when transferring information across institutions. In this manner, a user may perform queries on patient groups from multiple institutions via federated engine front-end 1120.

FIG. 12 is a simplified diagram of a method 1200 for information retrieval using a cohort analysis system, such as system 1000 or 1100, according to some embodiments. Illustratively, in the context of a clinical or pharmacological application, a user's interest with respect to clinical patient data may include of iteratively specifying, discovering and examining patterns in cohorts meeting specific clinical predicates that are relevant to his or her own context, and then using tools to analyze cohorts or compare them to other cohorts to make statistically sound inferences. Accordingly, method 1200 may facilitate these and other user objectives.

At a process 1210, user query associated with a clinical predicate P is received. A clinical predicate P includes a logical combination of one or more conditions on clinical patient data that arises in a patient event sequence E. For example, the patient event sequence E may include a sequence of timestamped events (e.g., rows of data table 600) corresponding to a particular patient and ordered in time. Each patient event sequence E may include one or more sub-sequences denoted e. An example of a clinical predicate E is as follows: if the user is seeking patients for whom diagnosis_code field has a value of X and medication_adminstered has a value of Y then we may deem the clinical predicate P in this instance to be diagnosis_code=X AND medication_administered=Y. The clinical predicate E may additionally or alternately include temporal or other types of constraints. An example of a temporal constraint is as follows: drug Y has to have been administered within 2 weeks of disease X. Another example of a constraint is as follows: patient must have a median value of v for a lab test measurement L over at least w repeats of the lab test over 3 months.

The user query may be provided in any suitable form. For example, the user query may include one or more keywords (like an internet search query) relevant to the clinical predicate P or a natural language description of the clinical predicate P. In some embodiments, the user may input a structured query format that explicitly indicates a logical combination of text keywords, clinical data field names, their specified values or value ranges, along with temporal constraints or other constraints.

At a process 1220, one or more clinical predicate candidates P1, P2, P3, . . . are determined based on the user query. In some embodiments, the clinical predicate candidates may be determined based on a semantic analysis of the user query. The clinical predicate candidates may be ranked in order of likelihood that a given candidate matches the user intended clinical predicate.

At a process 1230, the one or more clinical predicate candidates P1, P2, P3, . . . are presented to the user, e.g., as a list. In some embodiments, the clinical predicate candidates P1, P2, P3, . . . may be presented to the user as user-friendly clinical predicate descriptors Desc(P1),Desc (P2), Desc(P3), . . . . A given descriptor Desc(P) may correspond to one or more text (e.g., natural language text) or graphics that provide an unambiguous description of the clinical conditions corresponding to P. In some embodiments, the descriptor Desc(P) may be generated using a rule-based approach.

At a process 1240, a selection of a clinical predicate P among candidates P1, P2, P3, . . . is received from the user. To the extent the user determines that none of candidates P1, P2, P3, . . . is suitable, the user may refine the query and return to process 1210 until a suitable clinical predicate P is identified.

At a process 1250, a cohort C matching clinical predicate P is identified. In general, a cohort C corresponds to a group of patients who satisfy the clinical predicate P. For example, the cohort C may include the set of patient event subsequences e matching the clinical predicate P, obtained by considering the patient event sequences of the available patient data.

At a process 1260, a dashboard Dash(C) is presented to the user based on the cohort C. The dashboard Dash(C) provides an interactive interface to the user for analyzing clinical patient data associated with the selected cohort C. The dashboard Dash(C) may include one or more of the following modules: an indicator that displays the clinical predicate descriptor Desc(P) of the clinical predicate P that the cohort C matches; tools to modify the cohort C, e.g., tools to expand or reduce the cohort size by specifying addition conjunction or disjunction constraints in addition to the clinical predicate P that the cohort C matches; tools to persist the session or its underlying data for later use, such as tools download clinical patient data associated with cohort C; tools to run comparative statistical analysis with respect to other pre-defined cohorts C1, C2, C3, . . . (which may be selected using method 1200 or otherwise); or the like. Using these tools, the user may interacts with Dash(C), and may choose further operations offered in the dashboard with respect to cohort C. The user may then end the session or return to the original query to refine it, choose some other clinical predicate descriptor, or the like.

In some embodiments, the dashboard Dash(C) may include one or more clinical data widgets W(f1, C), W(f2, C), . . . . For example, a particular widget W(f,C) may include one or more graphical elements that represent one or more attributes of the values taken by the field(s) f in the patient data rows that belong to cohort C. In some embodiments, a field f may be directly available as part of the raw patient data provided by a given institution. However, as described previously with reference to FIG. 6, there are various limitations associated with the analysis of raw patient data. Accordingly, in some embodiments, a field f may be an augmented patient information field that is derived or mined from the raw patient data using, e.g., a knowledge graph or deep learning methods, such as the examples of augmented patient information depicted in data table 600.

An illustrative example of a widget W(f,C) is a table widget that displays a tabular summary of values off in the patient data rows that belong to cohort C. Additionally or alternately, a widget W(f,C) may display one or more tables, graphs, histograms, venn diagrams, or the like, which may be built from values taken by fields fin patient data rows belonging to cohort C. In some embodiments, a widget W(f,C) and/or the fields f1, f2, . . . may be pre-configured or configured by default such that it may be presented in response to a user query with low latency. In some embodiments, multiple widgets may be combined to form super-widgets, and the dashboard Dash(C) itself may be a super-widget.

As an illustrative and non-limiting example of method 1200, the user query received at process 1210 may include the term "hydroxychloroquine." This query may be analyzed, for example, using applications at layer 1030 of the cohort analysis system 1000. The analysis may use one or more tools, such as named entity recognition or a knowledge graph, to infer that the term "hydroxychloroquine" refers to a drug. Based on this inference, one of more of the following clinical predicate candidates may be determined and presented the user: patients whose physician notes mention "hydroxychloroquine"; patients whose physician notes indicate that they were administered "hydroxychloroquine"; patients who were administered "hydroxychloroquine" according to structured patient data's medications administered tables; or the like. In some embodiments, the term "hydroxychloroquine" may be expanded using the biomedical knowledge graph, e.g., by extending the query to other antimalarials (a drug class of which hydroxychloroquine is an instance).

In another illustrative example, the user query received at process 1210 may include the term "nmo." In this example, the system may infer that the term "nmo" refers to a disease. Based on this inference, one of more of the following clinical predicate candidates may be determined and presented the user: patients whose physician notes mention "nmo"; patients whose physician notes indicate that they were diagnosed with "nmo"; patients whose structured data diagnosis codes indicate the user was diagnosed with "nmo"; or the like. As above, the term "nmo" may be expanded using the biomedical knowledge graph, e.g., to include related diseases or conditions.

In another illustrative example, the user query received at process 1210 may include the term "sitagliptin AND type 2 diabetes." In this example, the system may infer that the query is a conjunction of a drug (sitagliptin) and a disease (type 2 diabetes). Based on this inference, one of more of the following clinical predicate candidates may be determined and presented the user: patients whose physician notes mention "sitagliptin" and "type 2 diabetes"; patients whose physician notes indicate that the physician sought to treat "type 2 diabetes" with "sitagliptin"; patients whose structured data diagnosis codes indicate the user was diagnosed with "type 2 diabetes" and was administered "sitagliptin"; or the like. As above, the terms "sitagliptin" and "type 2 diabetes" may be expanded using the biomedical knowledge graph, e.g., to include related drugs and diseases, respectively.

In some embodiments, a summary of cohorts C1, C2, C3, . . . matching each of clinical predicate candidates P1, P2, P3, . . . may be presented to the user at process 1230. The summary may include statistics associated with the cohorts C1, C2, C3, . . . , such as the number of patients in a particular cohort, the age, gender, or department distribution. In embodiments where the query is applied across a plurality of institutions (e.g., in a federated architecture that preserves patient privacy), the summary may identify the institution from which a given cohort arises.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

We claim:

1. A method comprising:

receiving, by one or more hardware processors, a specification of a patient cohort;

receiving, by the one or more hardware processors, a query;

receiving, by the one or more hardware processors, a plurality of documents from a corpus;

pre-processing, by the one or more hardware processors, the plurality of documents to extract data of a first format therefrom and remove data of a second format therefrom, wherein pre-processing the plurality of documents further comprises:

portioning the plurality of documents from the corpus into a plurality of shards, wherein for each shard of the plurality of shards, concatenating text of the each shard into a text array and generating an inverted list, wherein the inverted list is configured to identify positions of each occurrence of a token within a subset of the plurality of documents from the corpus;

expanding, by the one or more hardware processors, the query using a knowledge base to comprise one or more related terms to the query, wherein the one or more related terms to the query comprise a predetermined relationship with the query;

retrieving, by the one or more hardware processors, a list of search results based on the pre-processed plurality of documents, the expanded query and the specification of the patient cohort, each element in the list of search results comprising at least a portion of a clinical data record associated with a patient in the patient cohort;

computing, by the one or more hardware processors, one or more inferences for each item in the list of search results providing, by the one or more hardware processors, an aggregate statistical analysis associated with the one or more inferences; and providing, by the one or more hardware processors, a response to the query that includes the aggregate statistical analysis.

2. The method of claim 1, wherein the specification of the patient cohort comprises one or more parameters for identifying a group of patients, wherein the one or more parameters include at least one of a demographic, a diagnosis, a drug, a treatment plan, or a timeframe.

3. The method of claim 1, further comprising expanding, by the one or more hardware processors, the query to include one or more related terms, wherein the list of search results is retrieved based on the expanded query.

4. The method of claim 1, wherein the one or more inferences are computed using a machine learning model that identifies at least one of a sentiment or association based on the list of search results.

5. The method of claim 4, further comprising selecting, by the one or more hardware processors, the machine learning model from a plurality of machine learning models based on (a) the query and (b) metadata associated with the plurality of machine learning models.

6. The method of claim 1, further comprising comparing, by the one or more hardware processors, the list of search results associated with the patient cohort with a second list of search results associated with a second patient cohort.

7. The method of claim 6, wherein the list of search results is associated with a first institution and the second list of search results is associated with a second institution.

8. The method of claim 1, wherein receiving the specification of the patient cohort comprises:

receiving a user query;

determining one or more clinical predicate candidates based on the user query;

presenting the one or more clinical predicate candidates to the user;

receiving a selection of a clinical predicate among the one or more clinical predicate candidates; and identifying a cohort matching the selected clinical predicate.

9. The method of claim 8, wherein presenting the one or more clinical predicated candidates to the user comprises presenting one or more predicate descriptors corresponding to the one or more clinical predicate candidates.

10. The method of claim 8, wherein receiving the specification of the patient cohort further comprises ranking the one or more clinical predicate candidates in order of likelihood of matching an intended clinical predicate.

11. A system comprising:

a non-transitory memory; and one or more hardware processors configured to receive instructions from the non-transitory memory that, when executed, cause the one or more hardware processors to perform operations comprising:

receiving a specification of a patient cohort;

receiving a query;

receiving a plurality of documents from a corpus;

pre-processing the plurality of documents to extract data of a first format therefrom and remove data of a second format therefrom, wherein pre-processing the plurality of documents further comprises:

portioning the plurality of documents from the corpus into a plurality of shards, wherein for each shard of the plurality of shards, concatenating text of the each shard into a text array and generating an inverted list, wherein the inverted list is configured to identify positions of each occurrence of a token within a subset of the plurality of documents from the corpus;

expanding, by the one or more hardware processors, the query using a knowledge base to comprise one or more related terms to the query, wherein the one or more related terms to the query comprise a predetermined relationship with the query:

retrieving a list of search results based on the pre-processed plurality of documents, the expanded query and the specification of the patient cohort, each element in the list of search results comprising at least a portion of a clinical data record associated with a patient in the patient cohort;

computing one or more inferences for each item in the list of search results, providing an aggregate statistical analysis associated with the one or more inferences; and providing a response to the query that includes the aggregate statistical analysis.

12. The system of claim 11, wherein the operations further comprise expanding the query to include one or more related terms, wherein the list of search results is retrieved based on the expanded query.

13. The system of claim 11, wherein the one or more inferences are computed using a machine learning model that identifies at least one of a sentiment or association based on the list of search results.

14. The system of claim 13, wherein the operations further comprise selecting the machine learning model from a plurality of machine learning models based on (a) the query and (b) metadata associated with the plurality of machine learning models.

15. The system of claim 11, further comprising comparing the list of search results associated with the patient cohort with a second list of search results associated with a second patient cohort.

16. The system of claim 11, wherein receiving the specification of the patient cohort comprises:

receiving a user query;

determining one or more clinical predicate candidates based on the user query;

presenting the one or more clinical predicate candidates to the user;

receiving a selection of a clinical predicate among the one or more clinical predicate candidates; and identifying a cohort matching the selected clinical predicate.

17. The system of claim 16, wherein presenting the one or more clinical predicated candidates to the user comprises presenting one or more predicate descriptors corresponding to the one or more clinical predicate candidates.

18. A non-transitory computer-readable medium storing instructions that, when executed by one or more hardware processors, cause the one or more hardware processors to perform operations comprising:

receiving a specification of a patient cohort;

receiving a query;

receiving a plurality of documents from a corpus;

pre-processing the plurality of documents to extract data of a first format therefrom and remove data of a second format therefrom, wherein pre-processing the plurality of documents further comprises:

portioning the plurality of documents from the corpus into a plurality of shards, wherein for each shard of the plurality of shards, concatenating text of the each shard into a text array and generating an inverted list, wherein the inverted list is configured to identify positions of each occurrence of a token within a subset of the plurality of documents from the corpus;

expanding, by the one or more hardware processors, the query using a knowledge base to comprise one or more related terms to the query, wherein the one or more related terms to the query comprise a predetermined relationship with the query;

retrieving a list of search results based on the pre-processed plurality of documents, the expanded query and the specification of the patient cohort, each element the list of search results comprising at least a portion of a clinical data record associated with a patient in the patient cohort;

computing one or more inferences for each item in the list of search results providing an aggregate statistical analysis associated with the one or more inferences;

and providing a response to the query that includes the aggregate statistical analysis.

19. The non-transitory computer-readable medium of claim 18, further comprising comparing the list of search results associated with the patient cohort with a second list of search results associated with a second patient cohort.

20. The non-transitory computer-readable medium of claim 18, wherein receiving the specification of the patient cohort comprises:

receiving a user query;

determining one or more clinical predicate candidates based on the user query;

presenting the one or more clinical predicate candidates to the user;

receiving a selection of a clinical predicate among the one or more clinical predicate candidates; and identifying a cohort matching the selected clinical predicate.

* * * * *